United States Patent
Solorzano et al.

(10) Patent No.: US 11,203,151 B2
(45) Date of Patent: Dec. 21, 2021

(54) MULTI-HEADED AUTO-CALIBRATING BIOPRINTER WITH HEADS THAT HEAT, COOL, AND CROSSLINK

(71) Applicant: 3D SYSTEMS, INC., Rock Hill, SC (US)

(72) Inventors: Ricardo Solorzano, Philadelphia, PA (US); Eza Koch, Philadelphia, PA (US); Guillaume Robitaille-Beaumier, Montreal (CA)

(73) Assignee: 3D SYSTEMS, INC., Rock Hill, SC (US)

( * ) Notice: Subject to any disclaimer, the term of this patent is extended or adjusted under 35 U.S.C. 154(b) by 528 days.

(21) Appl. No.: 15/945,435

(22) Filed: Apr. 4, 2018

(65) Prior Publication Data

US 2018/0281280 A1      Oct. 4, 2018

Related U.S. Application Data

(60) Provisional application No. 62/481,305, filed on Apr. 4, 2017.

(51) Int. Cl.
   *B29C 64/209*       (2017.01)
   *A61L 27/52*        (2006.01)
   (Continued)

(52) U.S. Cl.
   CPC ............ *B29C 64/209* (2017.08); *A61L 27/52* (2013.01); *B29C 64/106* (2017.08);
   (Continued)

(58) Field of Classification Search
   CPC .................................................... B29C 64/209
   See application file for complete search history.

(56) References Cited

U.S. PATENT DOCUMENTS 5,572,431 A      11/1996   Brown et al.
5,795,390 A  *    8/1998   Cavallaro ........... B05C 11/1034
                                              118/314
(Continued)

FOREIGN PATENT DOCUMENTS

PT           104247 B      4/2009
WO      2012115334 A1      8/2012
(Continued)

OTHER PUBLICATIONS

Matti Kesti, "Development of 3D Bioprinting Inks Based on Tandem Crosslinked Hydrogels," 2013, Tampere University of Technology, 58 pages (Year: 2013).*

(Continued)

*Primary Examiner* — Monica A Huson
*Assistant Examiner* — Kelsey C Grace
(74) *Attorney, Agent, or Firm* — DLA Piper LLP US

(57) ABSTRACT

The present invention relates to a three-dimensional bioprinter for printing and/or patterning a single type or multiple types of cells into different geometrical arrangements and other three-dimensional structures, such as tissues. The bioprinter comprises multiple heads that can each be loaded with a different cartridge containing a biomaterial or biological material such as cells in a solution or cells in a hydrogel. Each bioprinter head and cartridge has the ability to heat or cool using Peltier technology. The bioprinter also has the ability to auto calibrate on a bed plate configured to accept a petri dish or microtiter plate.

23 Claims, 16 Drawing Sheets

(51) Int. Cl.

| | |
|---|---|
| *B29C 64/106* | (2017.01) |
| *B29C 64/112* | (2017.01) |
| *B29C 64/295* | (2017.01) |
| *B33Y 30/00* | (2015.01) |
| *C12M 3/00* | (2006.01) |
| *C12N 5/00* | (2006.01) |
| *C12N 5/071* | (2010.01) |
| *B29C 64/336* | (2017.01) |
| *B29C 64/25* | (2017.01) |

(52) U.S. Cl.
CPC .......... *B29C 64/112* (2017.08); *B29C 64/295* (2017.08); *B29C 64/336* (2017.08); *B33Y 30/00* (2014.12); *C12M 21/08* (2013.01); *C12N 5/0062* (2013.01); *C12N 5/0602* (2013.01); *B29C 64/25* (2017.08)

(56) References Cited

U.S. PATENT DOCUMENTS

| | | | |
|---|---|---|---|
| 8,639,484 | B2 | 1/2014 | Wei et al. |
| 9,073,366 | B1 | 7/2015 | Din et al. |
| 9,315,043 | B2 † | 4/2016 | Murphy |
| 2003/0128267 | A1 | 7/2003 | Teung et al. |
| 2005/0270516 | A1 | 12/2005 | Cherala et al. |
| 2011/0165595 | A1* | 7/2011 | Catanzaro ............. B01L 7/52 435/7.21 |
| 2011/0249699 | A1 † | 10/2011 | Bieberich |
| 2015/0037445 | A1 | 2/2015 | Murphy et al. |
| 2015/0105891 | A1 † | 4/2015 | Golway |
| 2015/0375453 | A1 † | 12/2015 | Yost |
| 2016/0023467 | A1 | 1/2016 | Din et al. |
| 2016/0193785 | A1 | 7/2016 | Bell et al. |
| 2016/0288414 | A1* | 10/2016 | Ozbolat ............... C09D 11/38 |
| 2017/0172765 | A1 | 6/2017 | Solorzano et al. |

FOREIGN PATENT DOCUMENTS

| | | |
|---|---|---|
| WO | 2015/148646 A2 † | 10/2015 |
| WO | 2015148646 A2 | 10/2015 |
| WO | 2015158700 A1 | 10/2015 |
| WO | 2017034951 A1 | 3/2017 |

OTHER PUBLICATIONS

International Search Report for International Application No. PCT/US2018/26090; International Filing Date: Apr. 4, 2018; dated Jul. 6, 2018; 3 Pages.

Written Opinion of the International Searching Authority for International Application No. PCT/US2018/26090; International Filing Date: Apr. 4, 2018; dated Jul. 6, 2018; 6 Pages.

Extended European Search Report in EP Application No. 18781772.1-1017/3606755, dated Feb. 1, 2021, 8 pages.

Jin-Hyung Shim, et al., "Bioprinting of a mechanically enhanced three-dimensional dual cell-laden construct for osteochondrial tissue engineering using a multi-head tissue/organ building system," J. Micromech. Microeng. 22 (Jul. 5, 2012) 085014, IOP Publishing (11 pages).†

Thomas Billiet, et al., "A review of trends and limitations in hydrogel-rapid prototyping for tissue engineering," Biomaterials 22 (Jun. 7, 2012) 6020-6041, Elesevier Ltd. (22 pages).†

Scott J. Hollister, "Porous scaffold design for tissue engineering," Nature Materials 4 (Jul. 2005) 518-524 and errata, Nature Publishing Group (8 pages).†

Matti Kesti, "Development of 3d Bioprinting Inks Based on Tandem Crosslinked Hyrdrogels," Master's Thesis (Oct. 21, 2013) Tampere University of Technology (58 pages).†

* cited by examiner
† cited by third party

FIG. 13A-D

MULTI-HEADED AUTO-CALIBRATING BIOPRINTER WITH HEADS THAT HEAT, COOL, AND CROSSLINK

CROSS-REFERENCE TO RELATED PATENT APPLICATION

This U.S. patent application claims priority to U.S. Provisional Application No. 62/481,305 filed on Apr. 4, 2017, titled, "A 3D bioprinter with a rotating turret," the entire contents of which are hereby incorporated by reference.

FIELD OF INVENTION

The disclosed invention is in the field of bioprinting that allows for methods of biofabrication.

BACKGROUND

In today's age, machines have completely changed lives, ranging from the first computer to cellphones. However, the most precise and well-articulated systems remain those that nature has built. The human body is an example of one such system which remains to be re-engineered. Organ transplantation has existed since the mid-1800s when the first skin transplant was performed. Since that time, transplantation has exploded, resulting in the transplantation of an organ or even several organs simultaneously. Initially, organs only from living identical twins were transplanted. Soon thereafter organs were transplanted from living and deceased donors, provided that the patient and donor have close genetic similarities. A donor could be a family member or even a genetically compatible stranger. In fact, more than 600,000 transplants have occurred in the United States since 1988. The quest for donor tissues and organs is a slow and uphill battle and there are not enough donors. More than 6,000 people die each year due to organ failure. There are presently over 120,000 people in the U.S. alone on waiting lists for organs and many others experiencing chronic problems due to the long-term damaging effects of post-transplant immunosuppression. This has prompted significant research and tests on fabricating mechanical organs and transplanting tissue and organs from non-humans, neither of which has had much success.

Donor tissues, organs, and even animals are also used in the testing and evaluation of pharmaceutical drugs. In fact, in bringing a pharmaceutical drug to the market, it takes years of animal testing before clinical trials on humans may be performed. Animal testing is expensive and inefficient, particularly in situations where the pharmaceutical drug fails to make it to market. Therefore, engineered tissues can have a huge impact on increasing the economics of drug testing and can improve testing accuracy and translatability into humans.

Animal tissues and organs are incredibly complex, possessing multiple different compartments that communicate with each other, intricate microarchitecture within these compartments, and many different cell types within each compartment. Bioprinting involves recreating the 3D structure of a tissue are designed to mimic the architecture of the extracellular matrix in which cells are suspended. Additionally, cells themselves can be incorporated into these constructs.

Bioprinters are complex, expensive, and complicated. They were very inaccessible to researchers around the world and scientists did not know why they were valuable. Bioprinters have been shown to be powerful tools to print multicellular geometrically relevant constructs. Bioprinting platforms have also allowed scientists to think about how cells are arranged within a tissue and scientists begin to add designs to their cell culture to improve scientific results by increasing physiological relevance.

Thus, there is a huge need for devices, platforms, and solutions for printing and pattern cells into specific geometries to make either tiny tissues or large ones for either drug screening or medical devices for organ replacement. This will have an immense impact on the way we treat patients and conduct medicine around the world.

SUMMARY OF THE INVENTION

The present invention relates to bioprinters, particularly to three-dimensional (3D) bioprinters. The 3D bioprinters disclosed herein relate to a multi-headed bioprinter, so that a plurality of materials can be dispensed and printed. The bioprinters disclosed herein also allow for maintaining the printed materials at a set temperature, for example, at 4° C. or 37° C.

In one aspect, the present relates to a three-dimensional bioprinter. The three-dimensional bioprinter comprises a multi-headed printing system, wherein the multi-headed printing system comprises a plurality of cartridges, each of the cartridges mounted around a central motor. The three-dimensional bioprinter also comprises an engager configured to automatically engage one of the plurality of cartridges, wherein the engager comprises a mechanical, an electrical or a pneumatic mechanism. The three-dimensional bioprinter further comprises a top plate and a bottom plate, wherein the top plate and the bottom plate are configured to secure the plurality of cartridges.

In one embodiment, the central motor is mounted to the top plate and rotates the top plate around a central axis, wherein rotation of the top plate rotates the plurality of cartridges.

In another embodiment, the three-dimensional bioprinter further comprises a plurality of linear motion carriages, wherein one of the plurality of linear motion carriages secure and allow vertical movement of one of the plurality of cartridges.

In another embodiment, at least one of the plurality of cartridges comprises one or more temperature control units. In some embodiments, the one or more temperature control units comprises a heating unit, a cooling unit, a thermoelectric unit, a fan, or a combination thereof. The one or more temperature control units controls the heating unit, the cooling unit, the thermoelectric unit, and the fan using an electrical board that communicates with a central processing unit.

In one embodiment, each of the plurality of cartridges are configured to receive a composition, wherein the composition comprises a biomaterial, a biological material, a curable extrusion agent or a combination thereof. In some embodiments, the biological material comprises a cell, a cell lysate, a protein, a peptide, an antibody, a biochemical, a nucleic acid, a growth factor or a combination thereof. In other embodiments, the biomaterial comprises a hydrogel, a matrigel or a combination thereof.

In one embodiment, the three-dimensional bioprinter comprises an LED board at a bottom end of the plurality of cartridges, wherein the LED board produces electromagnetic radiation greater than 405 nm.

In one embodiment, the plurality of cartridges are sized and configured to receive a delivery device. For example, in one embodiment, the delivery device is a syringe. In another embodiment, the plurality of cartridges are configured to dispense the composition at a volume between about 0.1 µl to about 1000 µl. In another embodiment, the plurality of cartridges are configured to extrude the composition continuously for about 0.1 seconds to about 2 days. In another embodiment, the plurality of cartridges are configured to extrude the composition continuously or non-continuously for about 0.01 seconds to about 10 days.

In one embodiment, the three-dimensional bioprinter further comprises a piston and a level arm connected to the piston, wherein vertical movement of the piston creates an internal pressure in an engaged cartridge between about 0.1 psi to about 250 psi.

In one embodiment, the three-dimensional bioprinter further comprises a central canister, wherein the central canister is housed within a central portion of the cartridge. In another embodiment, the central canister comprises a heat transfer material, wherein the heat transfer material comprises copper, aluminum, or nickel.

In another embodiment, the three-dimensional bioprinter comprises one or more heat sinks, one or more fans, or a combination thereof, attached to one of the plurality of cartridges. For example, the heat sinks can be of any appropriate size, e.g., 1 mm×1 mm or 10 mm×10 mm. Also, the heat sinks can have 5 to 1000 blades. The heat sinks can also comprise any material that allows for good heat transfer, such as copper, aluminum, or nickel, that can allow heat to transfer from the center canister to the fans to be dissipated into the environment.

In one embodiment, the three-dimensional bioprinter comprises an insulated electronics board, wherein the electronics board controls the one or more temperature control units. In some embodiments, the insulated electronics board can comprise an insulation comprising a high resistive plastic, a synthetic fiber, or an air insulation.

In another aspect, the present invention relates to a three-dimensional bioprinter comprising a multi-headed printing system, wherein the multi-headed printing system comprises a plurality of cartridges, each of the cartridges mounted around a central motor. The three-dimensional bioprinter further comprises an engager configured to automatically engage one of the plurality of cartridges, wherein the engager comprises a mechanical, an electrical or a pneumatic mechanism, a bed plate, a top plate, and a bottom plate. In one embodiment, the top plate and the bottom plate are configured to secure the plurality of cartridges.

In one embodiment, the bed plate comprises a recessed area sized and/or configured to accommodate a receiving device. The recessed area secures the receiving device on the bed plate so that the receiving device does not slide or otherwise move on the bed plate while any of the bioprinter components move in an x, y, or z direction. In one embodiment, the receiving device is a microtiter plate, a petri dish, or a glass slide. For example, the microtiter plate is a 6-, 12-, 24-, 48-, 96-, 384-, or 1536-well plate. Also, the petri dish is a 50 mm, 100 mm, or a 300 mm petri dish.

In another embodiment, the bed plate comprises temperature control unit. The temperature control unit comprises a source to heat or cool via with thermal heating, thermo electric cooling, liquid heating, liquid cooling, and/or electrical heating. This heating can control the temperature of the construct being creating in the receiving device.

In another embodiment, the bed plate comprises an auto-calibration system, wherein the auto-calibration system comprises one or more electrical pads. In another embodiment, the auto-calibration system in the bed plate comprises a mechanical switch or an optical sensor.

Other aspects of the present invention comprise a three-dimensional bioprinter comprising a 2, 3, 4, 5, or 6 headed mechanism (i.e., a multi-headed mechanism) that comprises 2, 3, 4, 5, or 6 individual cartridges. The cartridges can be loaded with an extrusion material or composition such as cells in a solution or cells in a hydrogel. The multi-headed mechanism sits on a 3 axis gantry system that moves in x and y directions along a Cartesian coordinate system. The multi-headed mechanism dispenses material on a bed plate that moves in the z direction.

In another aspect, the multi-headed mechanism contains a mechanism to be able to load and unload a cartridge and dispense the material. There is a mechanism that moves vertically in the z direction that engages the cartridge and the system that engages also contains a method to deliver a force mechanism. A pneumatic or mechanical force is applied to extrude the contents of the cartridge.

In a further aspect, the bioprinter contains a single (i.e., one) head and holds a single cartridge. Pneumatic or mechanical force can be used to extrude the contents of the cartridge. In another aspect, the bioprinter contains a different number of heads. The heads are engaged either in an automated fashion with a rotational mechanism or can be manually engaged. In another aspect, the bioprinter contains a plurality of heads and can be manually engaged or disengaged with the mechanism that engages or disengages the cartridge and pushes the material with either pneumatic or mechanical force to extrude the contents of the cartridge.

In yet another aspect, a single cartridge contains a method to heat or cool the specific the interior contents, for example, using Peltier technology. One or more fans are used to control the flow of heat whether towards or away from the cartridge.

In a further aspect, collagen or matrigel with cells are printed into multiple well plates (microtiter plates) e.g., for pharmaceutical screening. Collagen or matrigel can also be used to create tissues e.g., for pharmaceutical screening or medical devices.

In another aspect, a bed plate for the bioprinter has a specific cut out or a recessed area on the bed plate for well plates (microtiter plates), petri dishes, glass slides and the like. It also contains a location for the ability to autocalibrate.

In a further aspect, a method of testing a chemical agent is provided and includes (i) applying the chemical agent to a cellular structure prepared using the bioprinter described herein; and (ii) measuring the viability of the cells in the cellular structure.

In still yet a further aspect, a method for transplanting a synthetic organ in a mammal is provided and includes transplanting a cellular construct prepared using the bioprinter described herein to the mammal.

The general description and the following detailed description are exemplary and explanatory only and are not restrictive of the invention, as defined in the appended claims. Other aspects of the present invention will be apparent to those skilled in the art in view of the detailed description of the invention as provided herein.

BRIEF DESCRIPTION OF DRAWINGS

The summary, as well as the following detailed description, is further understood when read in conjunction with appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale.

DETAILED DESCRIPTION OF THE INVENTION

Figure 1:
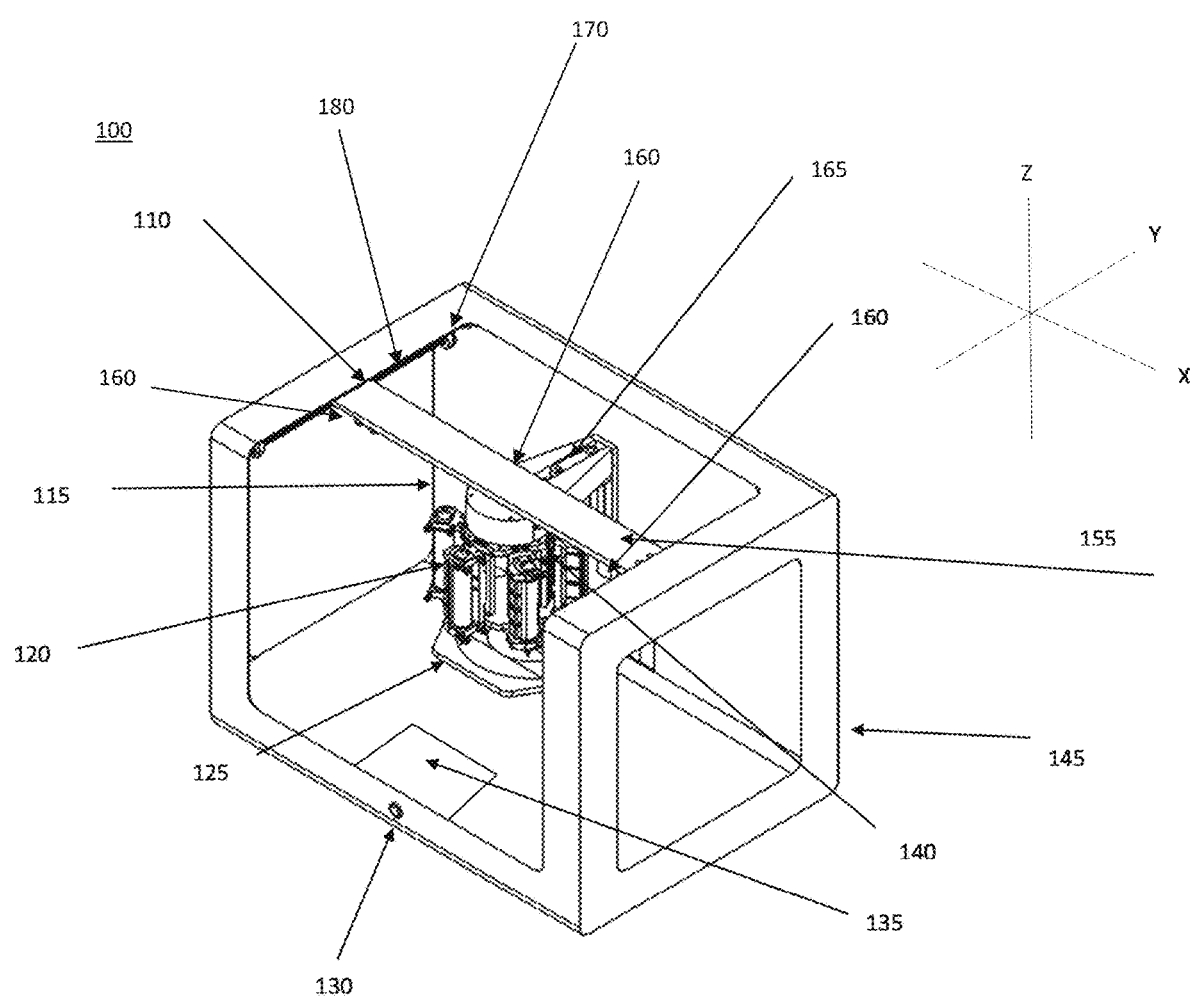
FIG. 1 illustrates a perspective view of an embodiment of a multi-headed bioprinter described herein on a Cartesian gantry system.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Similarly, unless otherwise stated, any description as to a possible mechanism or mode of action or reason for improvement is meant to be illustrative only, and the invention herein is not to be constrained by the correctness or incorrectness of any such suggested mechanism or mode of action or reason for improvement.

Also, as used in the specification including the appended claims, the singular forms "a," "an," and "the" include the plural, and reference to a particular numerical value includes at least that particular value, unless the context clearly dictates otherwise. Thus, for example, a reference to "a material" is a reference to at least one of such materials and equivalents thereof known to those skilled in the art, and so forth. The term "plurality," as used herein, means more than one. When a range of values is expressed, another embodiment includes from the one particular value and/or to the other particular value.

When a value is expressed as an approximation by use of the descriptor "about" or "substantially" it will be understood that the particular value forms another embodiment. In general, use of the term "about" or "substantially" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about" or "substantially". In other cases, the gradations used in a series of values may be used to determine the intended range available to the term "about" or "substantially" for each value. Where present, all ranges are inclusive and combinable. That is, references to values stated in ranges include every value within that range.

When a list is presented, unless stated otherwise, it is to be understood that each individual element of that list and every combination of that list is to be interpreted as a separate embodiment.

It is to be appreciated that certain features of the invention which are, for clarity, described herein in the context of separate embodiments, may also be provided in combination in a single embodiment. That is, unless obviously incompatible or excluded, each individual embodiment is deemed to be combinable with any other embodiment(s) and such any combinations is considered to be another embodiment. Conversely, various features of the invention that are, for brevity, described in the context of a single embodiment, may also be provided separately or in any sub-combination. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Finally, while an embodiment may be described as part of a series of steps or part of a more general structure, each said step may also be considered an independent embodiment in itself.

The present invention relates to bioprinters and printing components (e.g., biomaterials and biological material) as a two-dimensional and three-dimensional construct. The bioprinted materials can be formed into cellular constructs, tissues, organs, and other bioengineered constructs and are prepared using methods described herein. The methods involve utilizing technology based on three-dimensional, automated, computer-aided deposition of cells. In some embodiments, the bioprinters described herein are capable of generating tissues and organs. These structures can also not illicit an immune response. In such instances, these bioprinted tissues and organs would not require the administration of an immunosuppressants for transplantation. In some embodiments, the bioprinters are uncontaminated and do not contain infectious agents such as viruses, bacteria, and the like. The bioprinters described herein allow for the fabrication of bioengineered tissues and organs that obviate the need for organs from donors (i.e., other individuals). The bioprinters described herein also provide for fabricating these bioengineered structures in a cost effective manner since they are prepared from inexpensive biomaterials. The bioprinters also reduce or eliminate the need for animal testing of any new chemical, including pharmaceutical agents.

Bioprinter

In some aspects, the bioprinter may include any instrument that automates the bioprinting process described herein. In one embodiment, the bioprinter is a 3D printer, which may be selected by one skilled in the art. In one embodiment, the bioprinter is a 2D printer. In some embodiments, any component of the bioprinter described herein may be operated by manual and/or automatic (i.e., robotic) means.

In some aspects, the three-dimensional bioprinter comprises multiple components, including, for example a multi-headed printing system, an engager, a top plate and a bottom plate. The multi-headed printing system comprises a plurality of cartridges. Each of the cartridges are mounted around a central motor. The engager is configured to engage one of the cartridges, wherein the engager comprises a mechanical, an electrical or a pneumatic mechanism. The bioprinter allows for only one cartridge to be engaged at a time (e.g., while printing). However, there may be circumstances where more than 1, such as 2, 3, 4, 5, or 6 cartridges can be engaged simultaneously. The top plate and the bottom plate are configured to secure the plurality of cartridges. The central motor is mounted to the top plate and rotates the top plate around a central axis, wherein rotation of the top plate rotates the plurality of cartridges The bioprinter can contain one or more linear motion carriages housed within the interior of the bioprinter. Particularly, multi-headed printing system comprises a plurality of linear motion carriages, wherein one of the plurality of linear motion carriages secure and allow vertical movement of one of the plurality of cartridges. The one or more linear motion carriages permit a receiving device (e.g., a cartridge) to remain at a height needed to bioprint an article. The linear motion carriages may also be utilized to calibrate and/or level one or more components of the bioprinter, such as a cartridge. In one embodiment, the one or more linear motion carriages control movement of one or more components of the bioprinter including, without limitation, a cartridge, a bed plate, or any combination thereof. The movement of the linear motion carriages may be performed using skill in the art including, without limitation, a motor.

For example, in one embodiment, the one or more linear motion carriages are placed at a direction and/or a height and are of any width that is necessary to support one or more components of the bioprinter. In a further embodiment, the linear motion carriages are placed along the x-axis, y-axis, or z-axis, or any combination thereof in the bioprinter. In another embodiment, the one or more cartridges, a receiving device, a bed plate, or any combination thereof is attached to one or more linear motion carriages. In a further embodiment, the cartridge moves along the x and y axis and the bed plate moves along the z axis.

The one or more linear motion carriages housed within the bioprinter can also include one or more endstops. The one or more endstops are a means of defining a boundary to build the fabricated (e.g., bioprinted) article. The one or more endstops are also useful to keep one or more components of the bioprinter in a particular position. The one or more endstops may contribute to calibrating the position of one or more components on the respective x, y, and/or z axis. In one embodiment, the endstops ensure that the cartridge stays within the area of the receiving device. In another embodiment, the x and y endstops define the boundary for the cartridge. Accordingly, the x and y endstops restrict the movement of the cartridge to the size (e.g., dimensions) of the receiving device (e.g., a microtiter plate or a petri dish). For example, the cartridge may hit an endstop and cannot proceed past this point, i.e., it stays within the area of the receiving device. In a further embodiment, the z endstop defines the boundary for the receiving device and/or bed plate. Accordingly, the z endstop assists in modulating the height of the receiving device. In this instance, the z endstop ensures that the bed plate and receiving device do not move too high. In doing so, the z endstop may prevent the receiving device from contacting the needle and damaging the syringe and/or the fabricated article. The endstops may be fabricated using any materials available in the art including, without limitation, glass, coated glass, plastic, coated plastic, metal, a metal alloy, gel, or any combination thereof.

The multi-headed printing system of the three-dimensional bioprinter comprises a plurality of cartridges. Each cartridge can comprise one or more temperature control units. A temperature control unit can be a heating unit, a cooling unit, a thermoelectric unit, or a fan. Each cartridge is configured to receive a composition, such as a biomaterial, a biological material, a curable extrusion agent or a combination thereof. Biological materials, for example, can comprise a cell, a protein, a biochemical, an antibody, a nucleic acid, a growth factor or a combination thereof. Biomaterials, for example, can comprises, a hydrogel, a matrigel or a combination thereof. The composition can be a mixture of a biological material and a biomaterial, e.g., cells in a hydrogel. A source of electromagnetic radiation (e.g., an LED board) can be at or near a bottom end of a cartridge. If there are more than one cartridge (i.e., a plurality of cartridges), a source of electromagnetic radiation is optionally provided. For instance, the LED board can produce electromagnetic radiation less than about 405 nm or greater than about 405 nm Each cartridge of the multi-headed printing system is sized and configured to receive a delivery device. The delivery device can contain, store, or otherwise hold the composition, such as a biomaterial, a biological material, a curable extrusion agent or a combination thereof. For example, the delivery device is a syringe that be slide into and fit within the cartridge. The delivery device is configured to dispense the composition at any appropriate flow rate or volume for bioprinting. For example, the delivery device can dispense a composition between about 0.1 µl to about 1000 µl. Also, the delivery device can extrude the composition for any appropriate length of time. The time will depend on factors, including, flow rate, total volume of the delivery device (or cartridge), viscosity, temperature, and pressure. For example, the delivery device can extrude a composition (continuously or non-continuously) for about 0.1 seconds to about 5 days, about 1 second to about 2 days, about 1 minute to about 1 day, or about 1 hour to about 12 hours.

The multi-headed printing system of the three-dimensional bioprinter can further comprise a piston and a level arm connected to the piston. This arrangement allows for a vertical movement of the piston to create an internal pressure in an engaged cartridge. The internal pressure created by the system can be between about 0.1 psi to about 250 psi, about 0.2 psi to about 100 psi, about 1 psi to about 50 psi, or about 2 psi to about 20 psi.

The multi-headed printing system of the three-dimensional bioprinter can further comprise a central canister. The central canister is housed within a central portion of a cartridge. The central canister allows for heat exchange to and from the delivery device (or cartridge). So, the central canister comprises a heat transfer material, such as copper, aluminum, or nickel.

The multi-headed printing system of the three-dimensional bioprinter can further comprise one or more heat sinks, one or more fans, or a combination thereof. The heat sink(s), fan(s), or combination of heat sinks and fans, are attached to one the cartridges to allow for heating and/or cooling of the cartridge (or delivery device).

An electronics board controls the one or more temperature control units. The electronics board can be insulated or shielded from varying temperatures generated from the temperature control units. Any type of insulation or material can be used, such as, a high resistive plastic, a synthetic fiber, or an air insulation.

The three-dimensional bioprinter can further comprise a bed plate. The bed plate comprises a recessed area sized and configured to accommodate a receiving device. The receiving device is a microtiter plate, a petri dish, or a glass slide. The recessed area of the bed plate prevents movement of, for example, a microtiter plate during the bioprinting process. The bed plate can also comprise a temperature control unit. The temperature control unit can be a heating unit, a cooling unit, or both. The bed plate can further comprise an auto-calibration system, wherein the auto-calibration system comprises one or more electrical pads.

As noted above, one or more components of the bioprinter may be calibrated prior to or at one or more times during the bioprinting. Accordingly, the bioprinter contains a calibrating means for obtaining the proper level for one or more component. In one embodiment, one or more of the cartridge, bed plate, and/or receiving device is calibrated. In another embodiment, one or more component of the bioprinter is calibrated along one or more of the x, y, and z axes. Calibration of the bioprinter may be performed as described in U.S. Publication No. 2017/0172765, the entire contents of which are hereby incorporated by reference, using manual techniques, automated techniques, or a combination thereof. In one embodiment, the calibration means may include laser alignment, optical alignment, mechanical alignment, piezoelectric alignment, magnetic alignment, electrical field or capacitance alignment, ultrasound alignment, or a combination thereof.

FIG. 1 illustrates a perspective view of an embodiment of a bioprinter 100. Bioprinter 100 comprises x bar rail 110 that supports y bar 155. The y bar 155 sits on the x carriage 110 with two carriages, one on one side of the y bar 160 and one equally on the other side. Y bar 155 moves back and forth along the y axis (see reference XYZ axis) pushed by a motor 170 that lies on the back inside of the bioprinter 100. The Y carriage 175 then hosts the rotating extruder system 165 that is pushed by a motor 160. A rotating extruder 165 holds one or more cartridges 120 and rotates them using a motor 140 found on the center of the system. The cartridge systems 120 extrude onto a printing stage or bed plate 125. The printing stage 125 is configured such that it can hold a receiving means. For example, a receiving means can be any sized petri dish, glass slide, well plates, and the like. The bioprinter 100 can contain an interface 135 at the front location that allows the user to interact with it and an on and off (power) button 130. The printer can also comprise one or more cords for power, air flow, and/or a computer connection on the sides 145 or 115.

Still referring to FIG. 1, another aspect of the present disclosure is a procedure for calibrating one or more components of a bioprinter and includes use of one or more linear motion carriages 110, 155, 125.

In order to prepare the fabricated materials, the bioprinters disclosed herein control and dispense a composition (e.g., a biomaterial, a biological material or a combination thereof) with repeatable accuracy. In one embodiment, the position of the cartridge is calibrated along the x-axis, the y-axis, and the z-axis, or a combination thereof. The accuracy is dependent on a number of factors, including, without limitation, removal and insertion of cartridges, position of the cartridge, among others. Calibrating the position of the cartridge includes the use of a laser (e.g., auto-calibrated), visually (e.g., manually calibrated), or a combination thereof.

Figure 2:
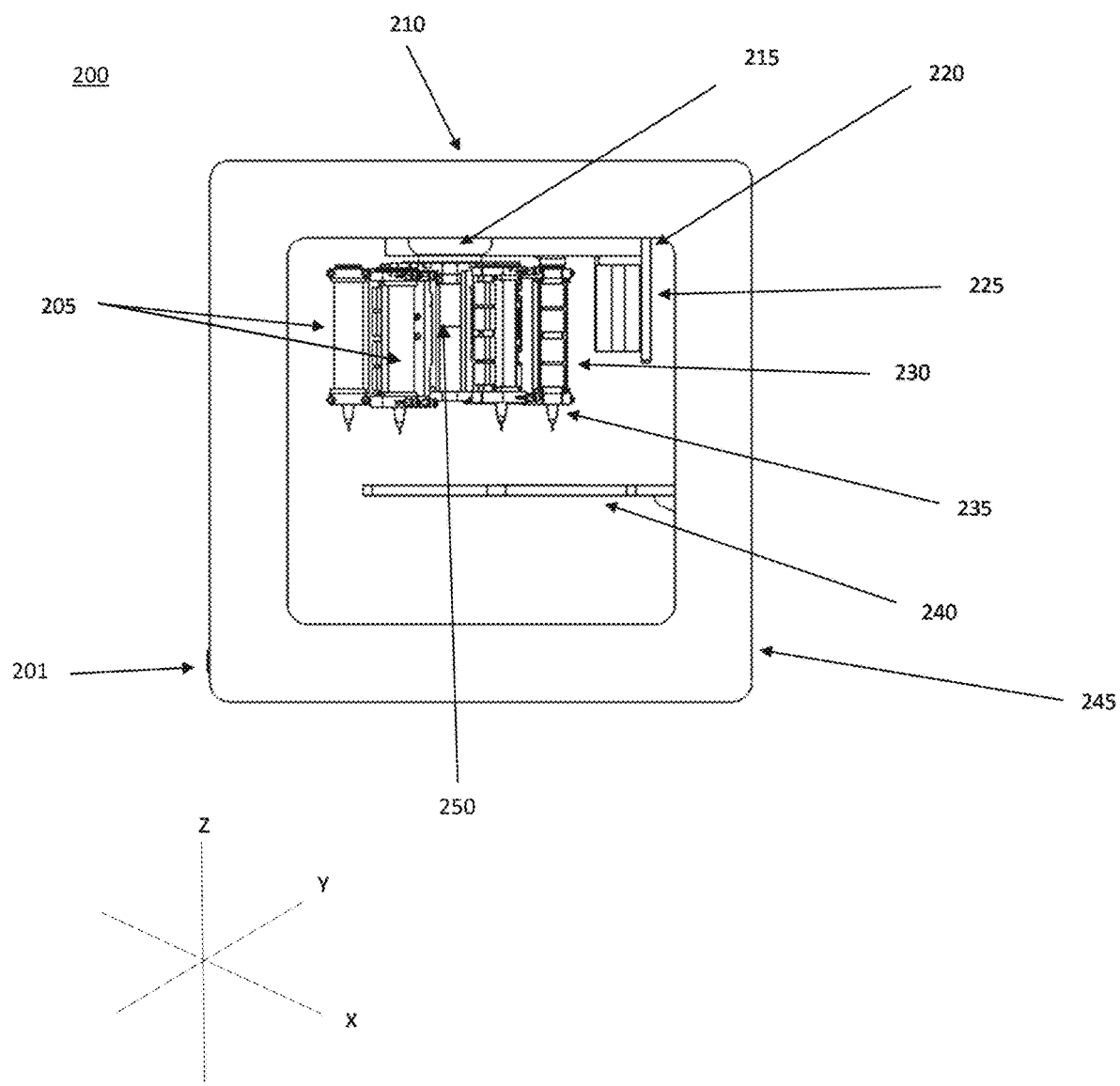
FIG. 2 illustrates a side view of an embodiment of a bioprinter comprising a multi-headed printing system, a bed plate, and a cartridge system that can control the temperature.

FIG. 2 illustrates an embodiment of a bioprinter from a side view. The bioprinter 200 can be interfaced with the on and off button or interface screen 201 found on the front of the bioprinter 200. The top of the printer houses an x and y axis system 210 that holds a rotating printing system 215. The rotating printing system 215 holds one or more cartridges 205 and also houses a center motor system 250 The middle 225 and top 220 backside of the rotating printing system 215 is the mechanism used to engage or disengage a cartridge 230 that has a loaded syringe with a needle 235. Cartridge 205 prints on a bed plate surface 240 that moves up and down in the z direction. The bioprinter 200 is contained within a housing 245.

The atmosphere of the bioprinter can be adjusted to provide optimal conditions for depositing the composition or biomaterial. Specifically, the temperature, humidity, atmospheric composition (i.e., gas composition), among others can be controlled and adjusted. In one embodiment, the bioprinter comprises a means for adjusting the temperature within the bioprinter. In some embodiments, the temperature of the individual bioprinter components, such as, for example, the cartridge and/or the receiving device are controlled. In some embodiments, multiple components of the bioprinter, including the atmosphere within the bioprinter are each controlled individually and independently. The temperature may be selected by one skilled in the art and may depend on the type of cell or biomaterial being printed. In one embodiment, the temperature is maintained at a temperature which results in a suitable physical environment for the cells. In one embodiment, the temperature is maintained at about −20° C. to about 300° C. In a further embodiment, the temperature is maintained at about 0° C. to about 100° C. In another embodiment, the temperature is maintained at about 10° C. to about 30° C. In another embodiment, the temperature is maintained at about 15° C. to about 25° C. In another embodiment, the temperature is maintained at about room temperature (i.e., about 21° C.). In another embodiment, the temperature is maintained at about 20° C. to about 50° C. In another embodiment, the temperature is maintained at about 30° C. to about 40° C. In another embodiment, the temperature is maintained at about 37° C. The means for maintaining the temperature within the bioprinter and/or components of the bioprinter at a certain temperature or within a range of temperatures can include a heating and/or cooling element. Heating elements include, without limitation, radiant, convection, conductive, fan, heat exchange heater, or any combination thereof. Cooling elements include, without limitation, coolant, chilled liquid, ice, a radiant cooler, convection cooler, a conductive cooler, a fan cooler, or any combination thereof. In one embodiment, the cooling system is a pelti temperature control device that regulates the flow of heat using fans and its controlled by an electronics board.

The humidity within the bioprinter or of the individual components including inside the cartridge can also be varied. Specifically, the humidity can be adjusted (i.e., be increased or decreased) as necessary. The humidity can range from about 0% to about 100%.

The gaseous (atmospheric) composition of the bioprinter, when sealed, can be varied and adjusted. In embodiments, the atmospheric conditions within the bioprinter can be similar to air (e.g., about 78% N2, about 21% O2, and about 1% Ar by volume). In other embodiments, the atmospheric conditions within the bioprinter can have varying concentrations of gas, including, but not limited to, carbon dioxide, nitrogen, argon, and oxygen. For example, the concentrations of CO2, N2, Ar, and O2 can each be adjusted from about 0% to about 100%.

Multi-Headed Rotating Printing System

The present invention is also directed towards a multi-headed rotating printing system. The multi-headed rotating printing system comprises a plurality of cartridges mounted around a central motor. The central motor spins the cartridge of interest into an engaged position. This allows for automatically engaging one of the cartridges and positioning it for extrusion. Once a cartridge is engaged, the engager can contain either pneumatic or mechanical method of extruding the contents out of the cartridge.

Figure 3:
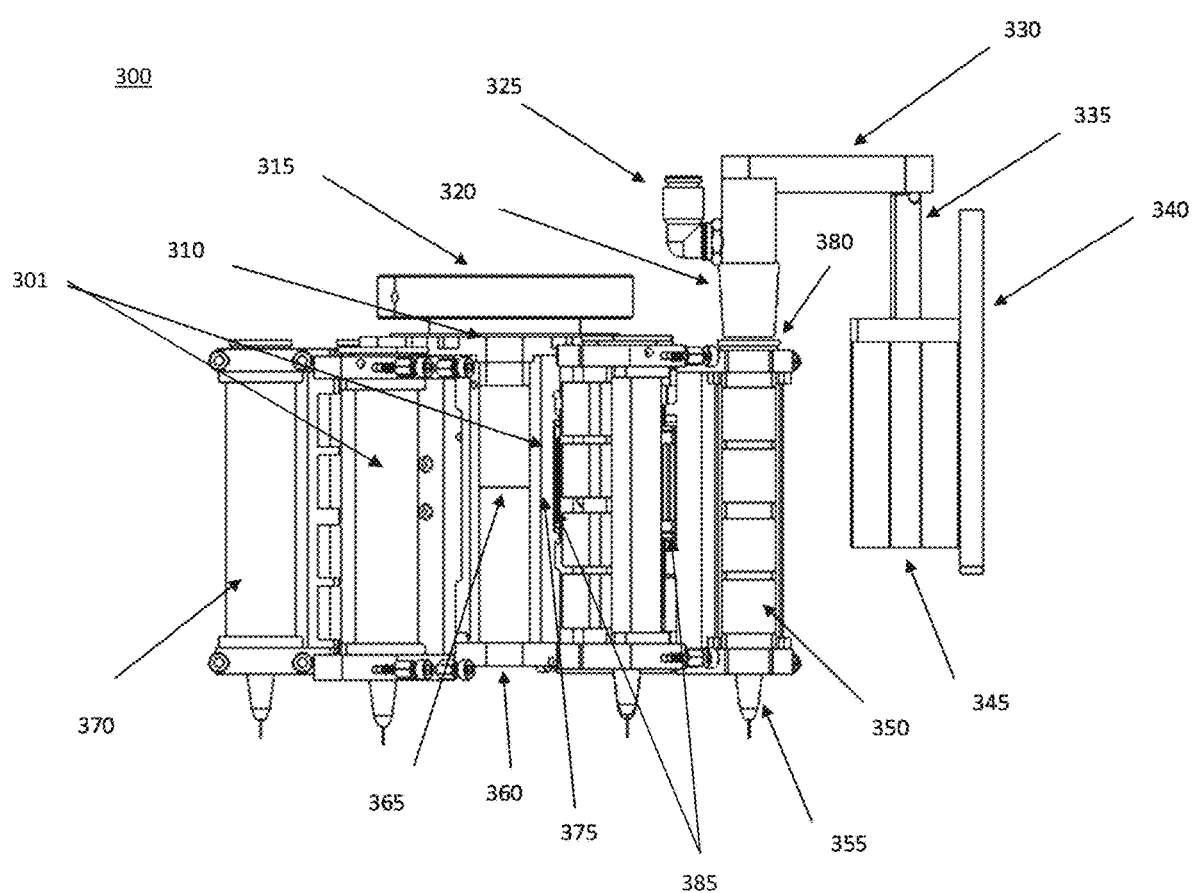
FIG. 3 illustrates a side view of an embodiment of a multi-headed printing system used to engage and disengage a cartridge system, in a disengaged configuration.

FIG. 3, illustrates an embodiment of internal components of a rotating printing system 300. The system 300 comprises a center bearing 315 at its core that keeps the rotating of the cartridges 301, 370, 350 aligned. There is a plate or a rail 375 that holds the carriages 385 of which the cartridges can slide up and down on depending on whether they are engaged or not 385. Top plate 310 moves in circular direction by force by a motor mounted under 365. The blocks that hold the cartridges 301, 370, 350 are held together by both the top plate 310 and the bottom plate 360. The engager 340 uses a mechanism to raise itself up and down using either mechanical or pneumatic pressure mechanism 345. Piston 335 moves up and down in sync and a lever arm 330 that supports the piston. Pneumatic air inlet 325 sends air down plunger 320 to a syringe 380 loaded in a cartridge. Creation of pneumatic force extrudes material out of the tip 355 of cartridge 301. The temperature within syringe 380 can be controlled by mounted one or more heaters and/or coolers and fans 350 alongside the center of a cartridge 301, 370, 350. For example, the one or more heaters and/or coolers is one or more pelti heaters and/or coolers.

Figure 4:
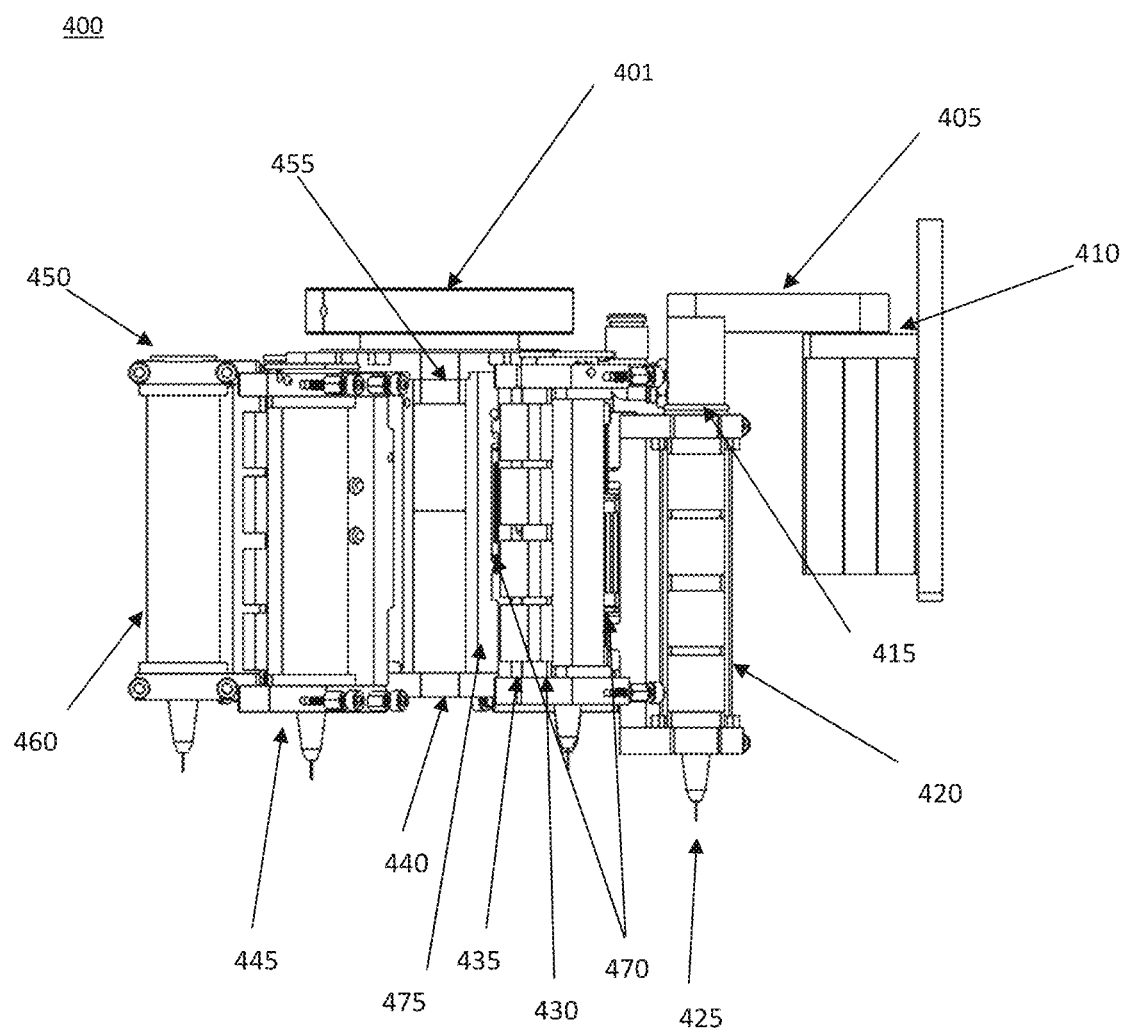
FIG. 4 illustrates a side view of an embodiment of a multi-headed printing system used to engage and disengage a cartridge system, in an engaged configuration.

FIG. 4 illustrates a rotating printing system 400 and its internal components in the engaged position. The system 400 at its core has a center bearing 401 that keeps the rotating of the cartridges 420, 445, 460 aligned. There is a plate 455 that is attached to the bearing 401 that holds the carriages 470 which the cartridges 420, 445, 460 slide up and down on depending on whether they are engaged or not. Top plate 455 moves in a substantially circular direction by a bi-polar motor mounted under top plate 455. The blocks 475 that hold the cartridges 470 are held together by both the top plate 455 and the bottom plate 440. The engager 415 uses a mechanism to raise itself up and down using either mechanical or pneumatic pressure. In an engaged position the piston 410 is compressed by either pneumatic or mechanical strain and translates the motion at a center piece 405. When engaged, the force down movement of the piston moves the entire cartridge 420, 445, 460 down by an equidistant amount. Then once moved down the contents can be dispensed out of 425. The cartridges 420, 445, 460 can control temperature through one or more heaters and/or coolers to influence the contents being held by the inner cartridge or syringe 415. For example, the one or more heaters and/or coolers is one or more pelti heaters and/or coolers.

Figure 5:
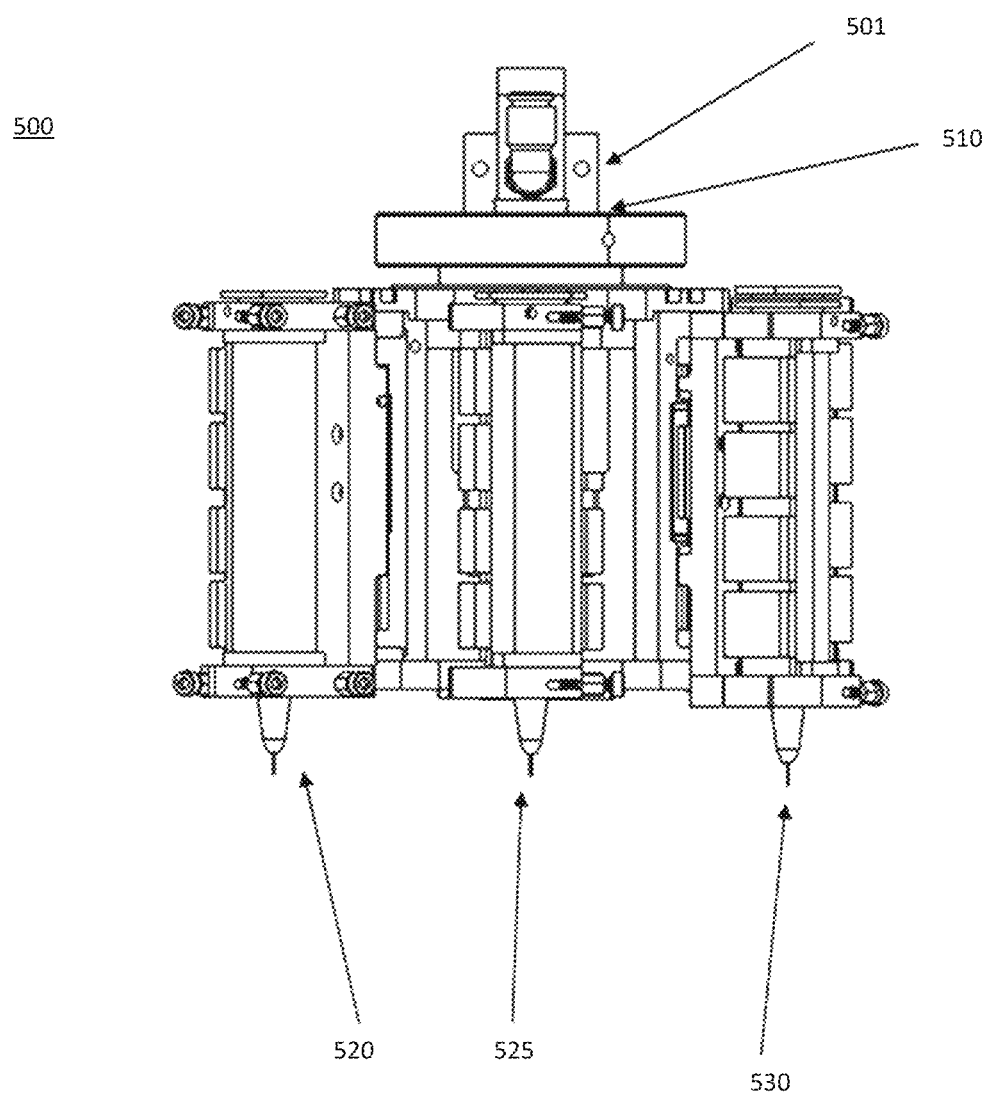
FIG. 5 illustrates a front view of an embodiment of a multi-headed printing system.

FIG. 5 illustrates a rotating printing system 500 and cartridges 520, 525, 535 arranged in a circular pattern around center bearing 510. It will be readily apparent to one of ordinary skill in the art that a maximum number of cartridges can fit around center bearing 510 with the engager 501. In some aspects, 1, 2, 3, 4, 5, 6, 7, 8, 9, 10, 11, or 12 cartridges are arranged around a center bearing. In some aspects, more than 1, more than 2, more than 3, more than 4, more than 5, more than 6, more than 7, more than 8, more than 9, or more than 10 cartridges are arranged around a center bearing. The mechanism houses a motor on the inside and is used to rotate the different cartridges to the cartridge of interest to be engaged by the dispensing mechanism.

Figure 6:
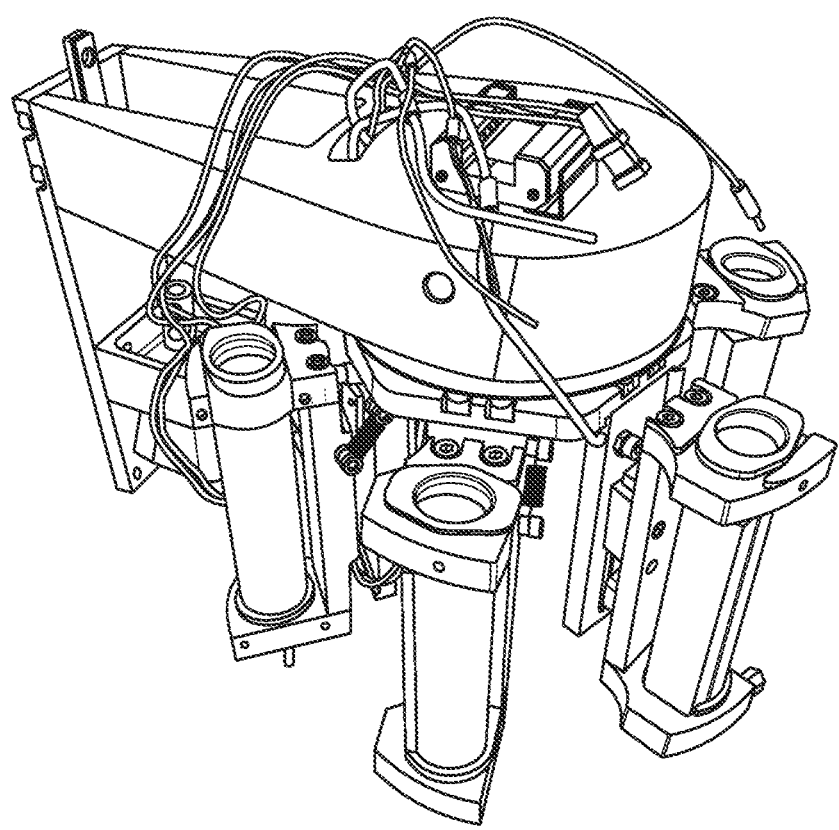
FIG. 6 is a photograph of a perspective view of an embodiment of a multi-headed printing system.

FIG. 6 illustrates an embodiment of a multi-headed rotating bioprinting systems machined and fully assembled.

Bed Plate (Printing Stage)

A bed plate is another component of the bioprinter described herein. The bed plate as used herein regulates the movement of the receiving device, as described below. In one embodiment, the printer plate moves the receiving device up and down. The bed plate may be, without limitation, glass, coated glass, plastic, coated plastic, metal, a metal alloy, gel, or a combination thereof. In one embodiment, the bed plate is square, circular, triangular, oval, rectangular, or irregularly shaped. In another embodiment, the bed plate has different cut outs to be able to secure different well plates or petri dishes. The bed plate can accommodate any sized well plates, such as, for example, 6, 12, 24, 48, 96, 384, 1084, or 3084-well plates.

Figure 7:
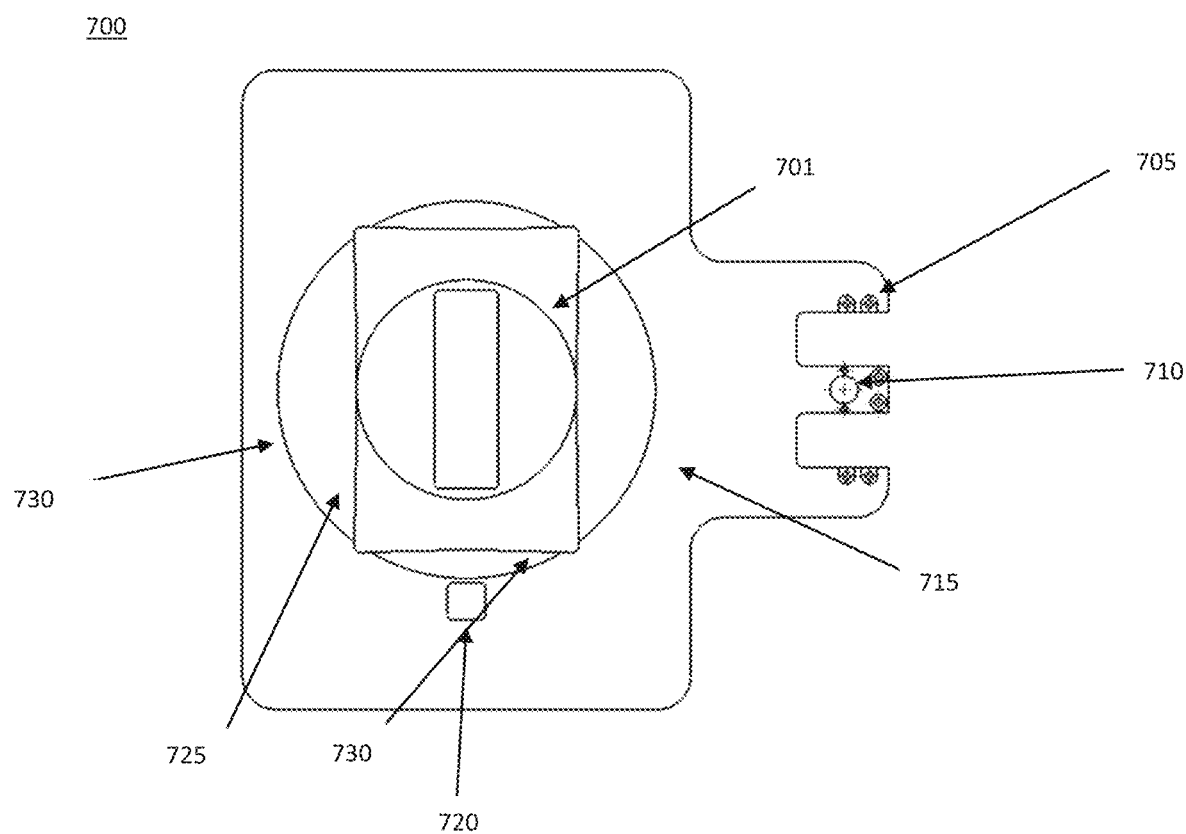
FIG. 7 illustrates a top view of an embodiment of a bed plate of the bioprinter, for receiving contents that are dispensed and auto-calibration of the bioprinter.

FIG. 7 illustrates a top view of a bed plate 700. Bed plate 700 is a printing stage that comprises a recessed area or cut outs sized and configured to hold and secure, for example, a small petri dish 701, a larger petri dish 730, well plates 725, a glass slide 715, or an auto-calibration system 720. One end 705 of the bed plate 700 contains screws to be able to mount and mate to the bioprinter system, and a center hole 710 to be able to attach to the Z motor to move up and down in the Z direction.

Figure 8:
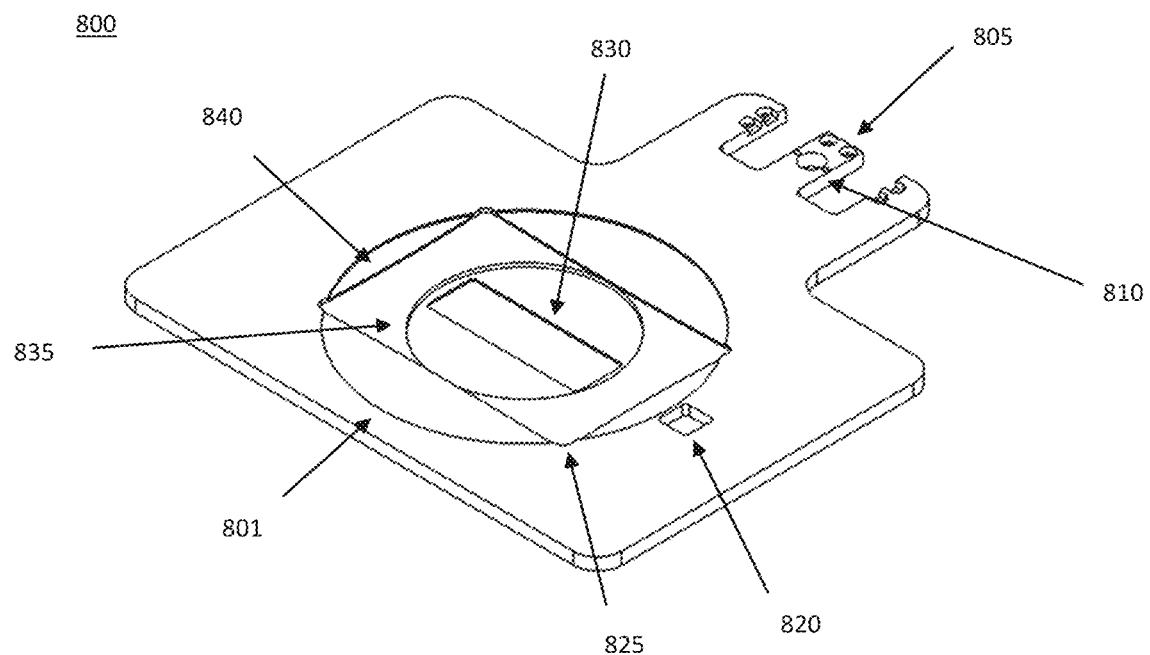
FIG. 8 illustrates a perspective view of an embodiment of a bed plate of the bioprinter for receiving contents that are dispensed and auto-calibration of the bioprinter.

FIG. 8 illustrates a perspective view of a bed plate 800. Bed plate 800 is a printing stage that comprises a recessed area or cut outs sized and configured to hold and secure, for example, a small petri dish 835, a large petri dish 801, a glass slide 830, or an auto-calibration system 820. Auto-calibration system 820 is a recessed area within bed plate 800 and can comprise one or more electrical pads. One end 805 of bed plate 800 contains screws to mate to a printer system, and a center hole 810 to be able to attach to the Z motor to move up and down in the Z direction.

Figure 9:
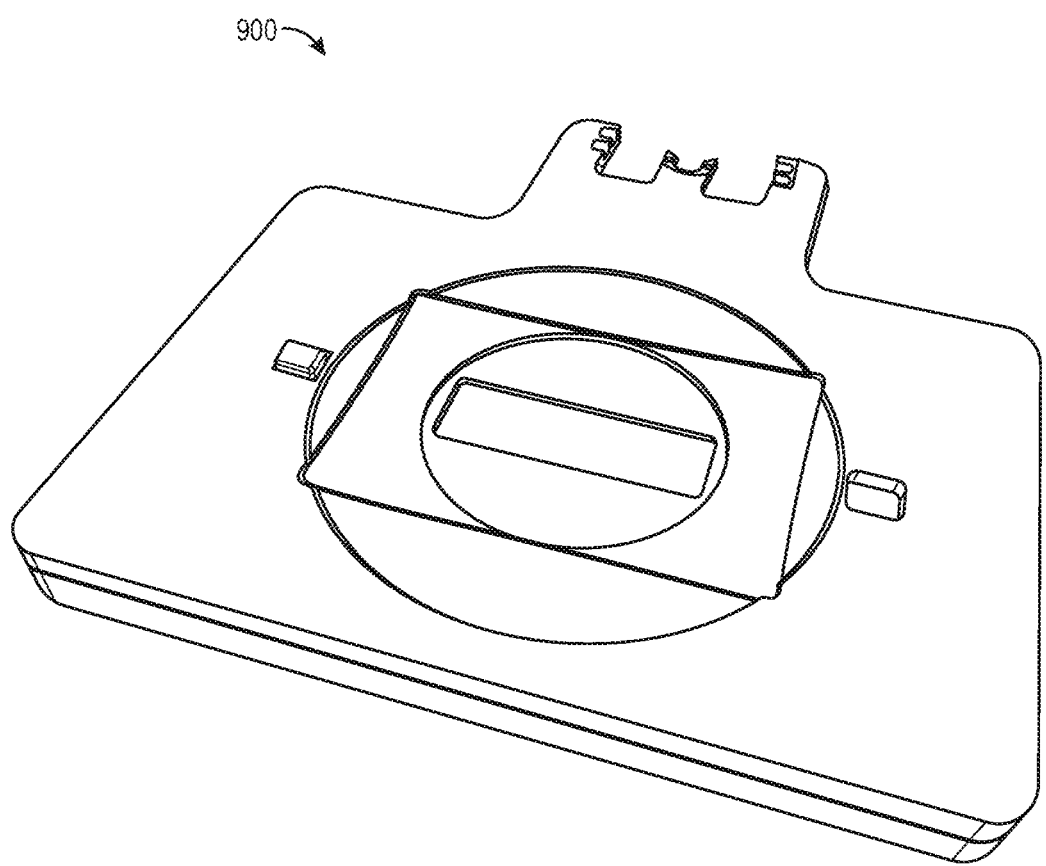
FIG. 9 is a photograph of a perspective view of an embodiment of a bed plate of the bioprinter.

FIG. 9 illustrates bed plate 900.

The bioprinter disclosed herein is capable of dispensing a composition in a predetermined geometry, i.e., position, pattern, and/or layer, in two or three dimensions, onto a receiving device (e.g., a microtiter plate or petri dish). In one embodiment, the receiving device is a receiving plate. In another embodiment, the receiving device has a 3D structure such as a tissue structure, gel, multi-well plate (e.g., microtiter plate), or a combination thereof. In another embodiment, the receiving device is a water bath. The receiving device can be any material, device, or component that can receive extruded and/or bioprinted materials from a cartridge.

Accordingly, the bioprinter achieves a particular geometry of the fabricated article by moving the cartridge relative to a receiving device. Alternatively, the receiving device is moved relative to the cartridge.

In an effort to reduce contamination, the receiving device is non-toxic to the biomaterial, components of the composition, or any combination thereof. The locations at which the bioprinter deposits the composition onto a receiving device are adjustable as determined by the user.

The receiving device is desirably designed specifically to accommodate the shape, size, texture, or geometry of the fabricated article. It may be flat or substantially flat; smooth or substantially smooth; defined or substantially defined; or any combination thereof. The receiving device may assume a variety of concavities, convexities, or topographies based on the article to be fabricated. The receiving device may contain, without limitation, glass, coated glass, plastic, coated plastic, metal, metal alloy, gel, or any combination thereof. The receiving device and the biomaterial may be biocompatible. In one embodiment, the receiving device is a substantially flat plate, multi-well plate such as a 6- or 96-well plate, or 3D scaffold in which the cartridge moves in 3 dimensions. In another embodiment, the receiving device is square, circular, triangular, oval, rectangular, or irregularly shaped.

The receiving device is located within the bioprinter and adjacent to the cartridge. The receiving device may also be adjacent to the bed plate. In one embodiment, the receiving device is positioned below the cartridge. In another embodiment, the receiving device is positioned above the printer driver. In a further embodiment, the receiving device is positioned between the cartridge and the bed plate.

The receiving device may be leveled prior to deposition of the composition. The leveling may be performed as described above by adjusting the bed plate using the rods and endpoints. Alternatively, the bioprinter could have a self-leveling means, thereby eliminating the need for human intervention for leveling the hardware. In doing so, software may be used to analyze the position of the receiving device and perform any necessary adjustments. In one embodiment, the receiving device is leveled to 0 relative to the flat bottom of the cartridge.

Cartridge and Cartridge System

Figure 10:
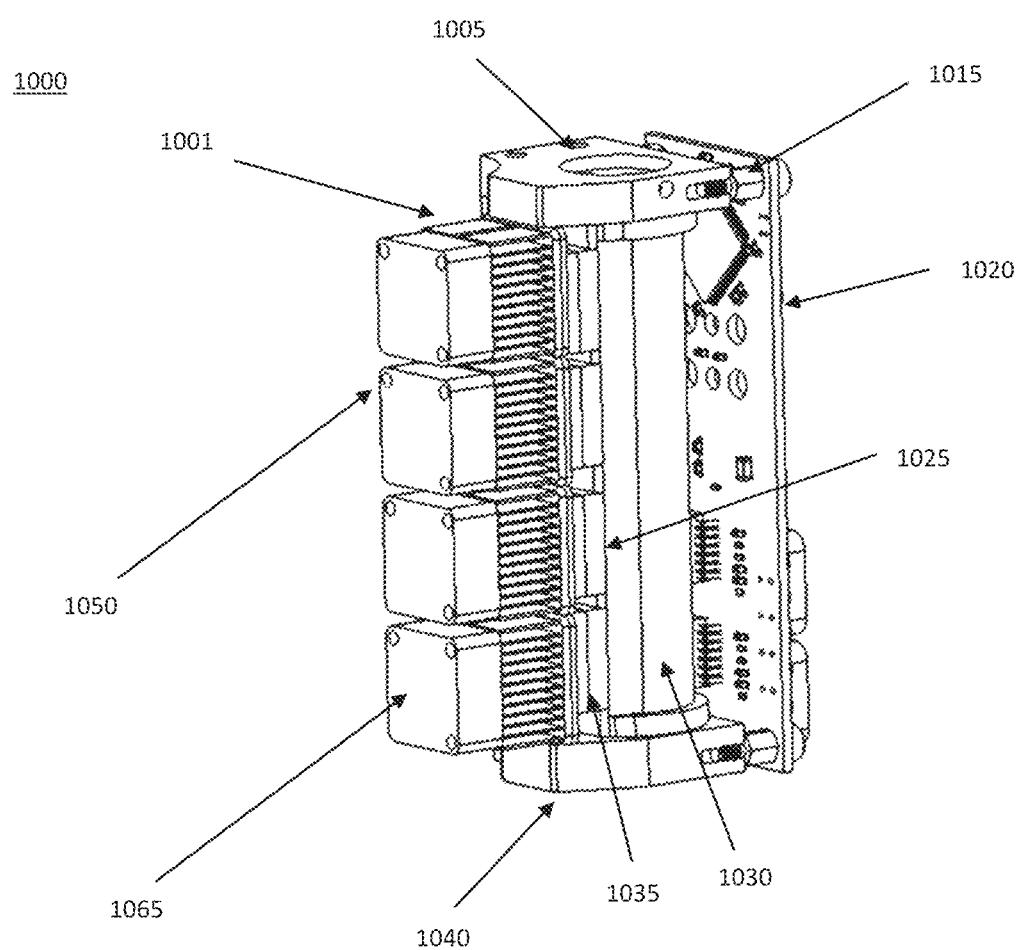
FIG. 10 illustrates a perspective view of an embodiment of a cartridge system and components used to control the temperature of the bioprinter.
Figure 11:
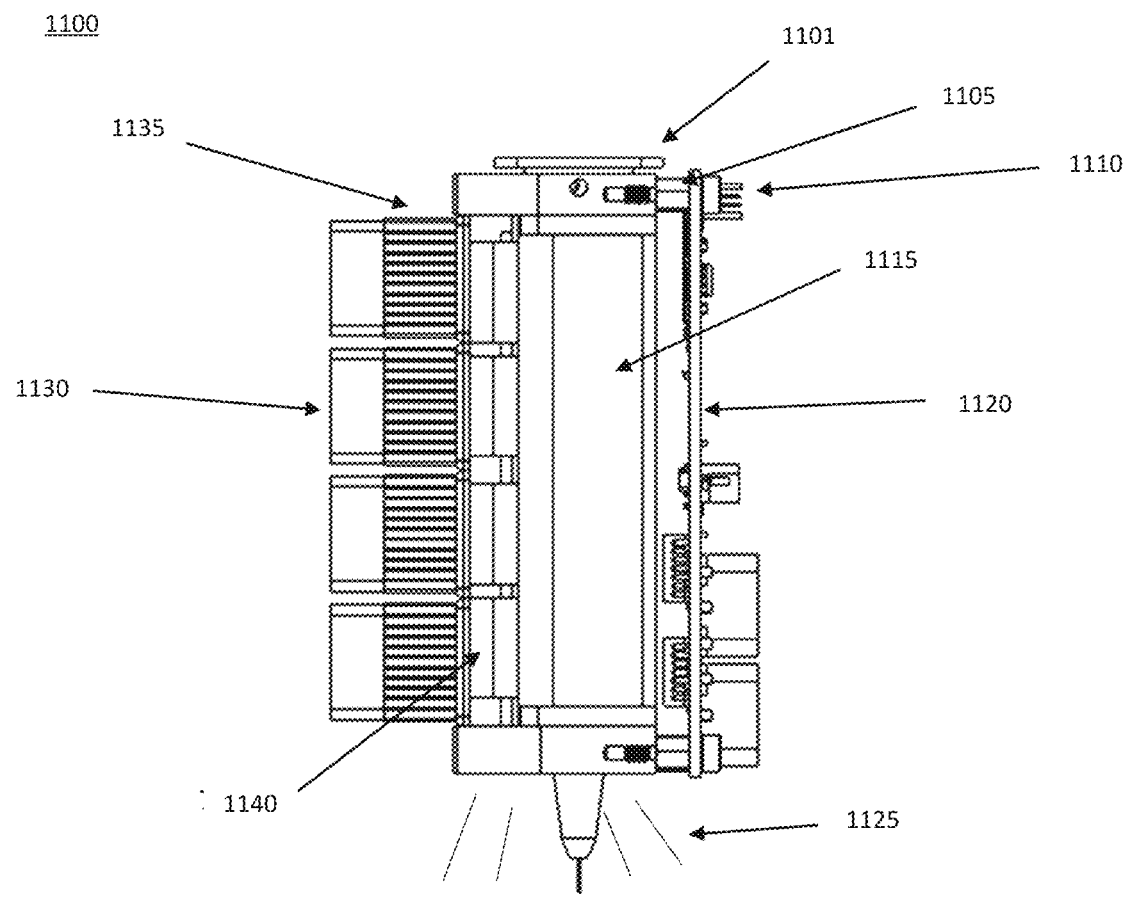
FIG. 11 illustrates a side view of an embodiment of a cartridge system of the bioprinter.
Figure 12:
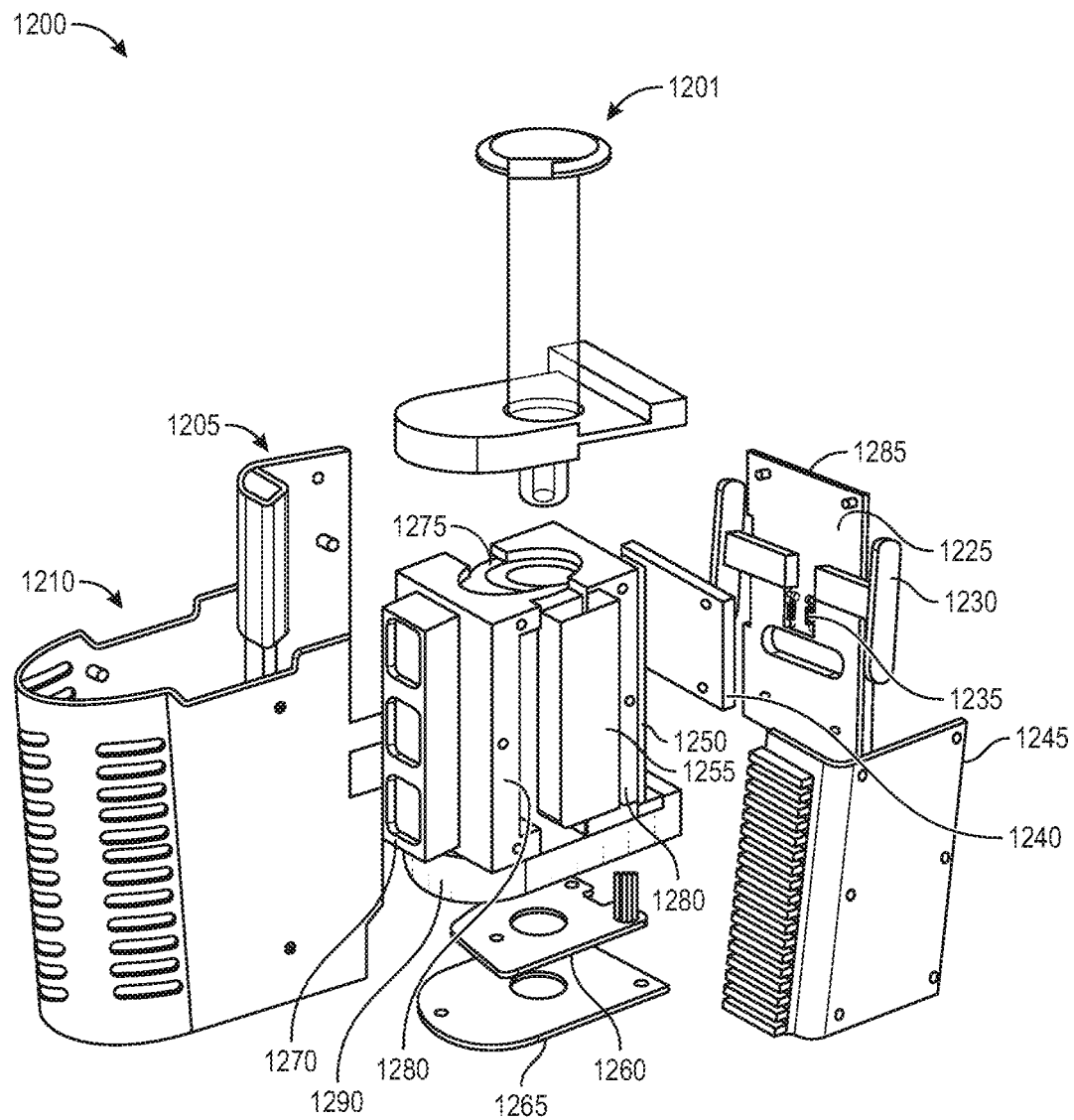
FIG. 12 illustrates an exploded view of an embodiment of a cartridge system of the bioprinter.
Figure 13:
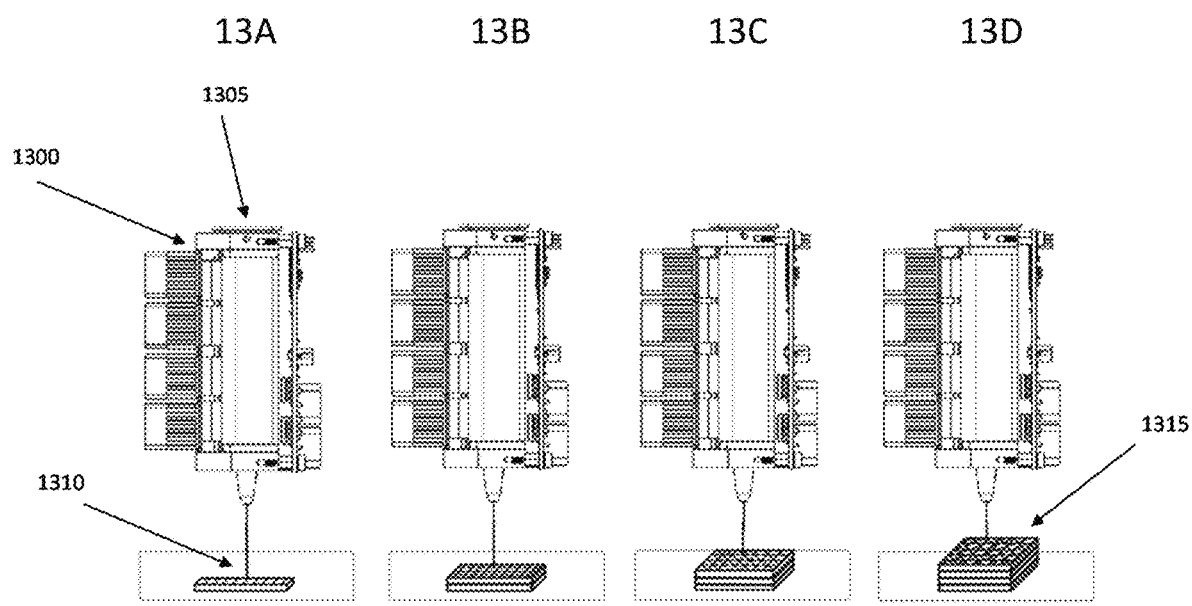
FIGS. 13A-D illustrate an embodiment of bioprinting using the methods described herein.
Figure 14:
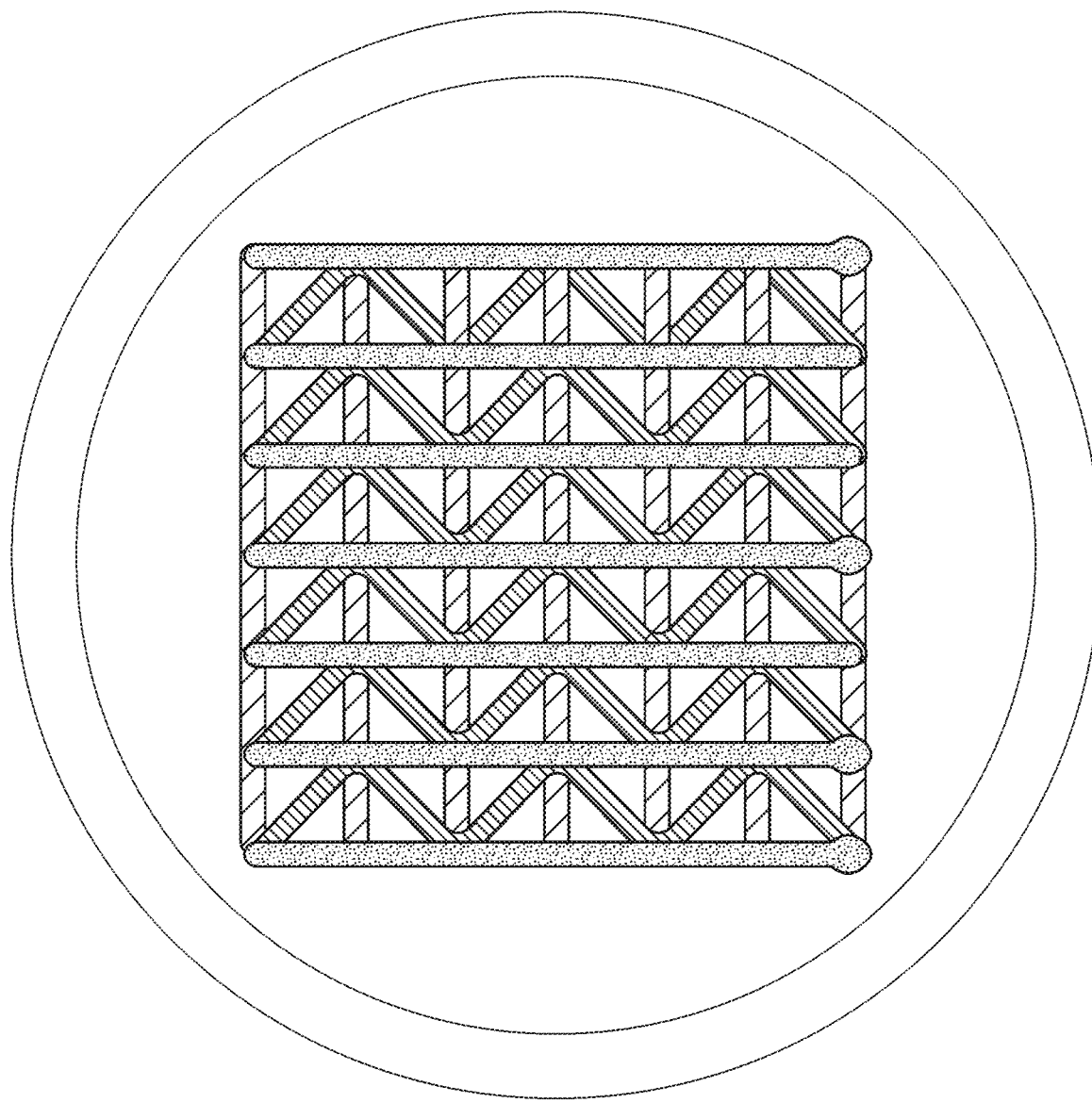
FIG. 14 is a photograph of an embodiment of a support construct printed using a bioprinter described herein.
Figure 15:
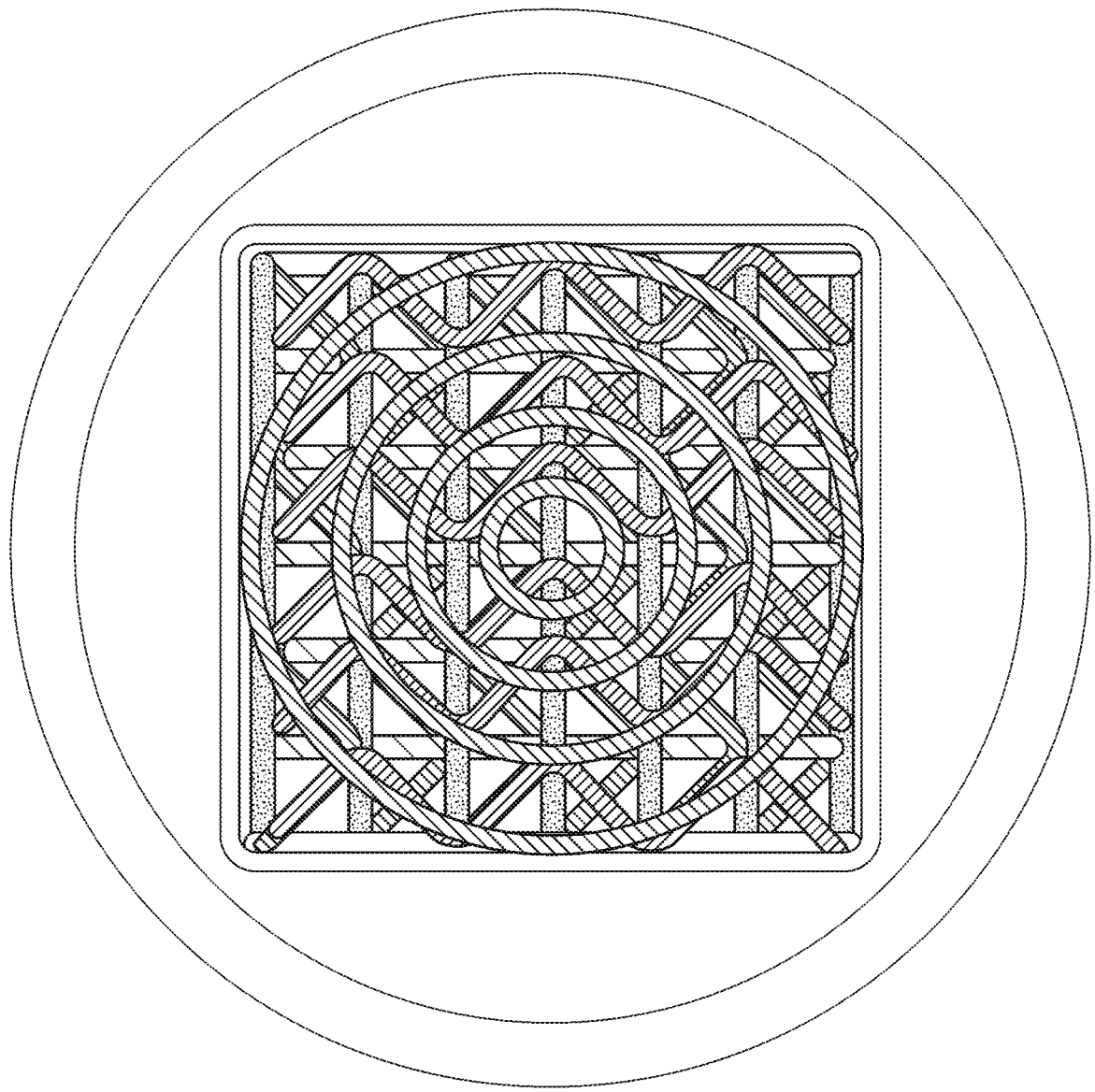
FIG. 15 is a photograph of another embodiment of a support construct printed using a bioprinter described herein.

As used herein, a "cartridge" is any object that is capable of receiving and holding a composition prior to deposition described herein. Referring to FIGS. 10-12, the cartridge may be attached to the bioprinter using any means known in the art. Any number of cartridges may be utilized and the number of cartridges used depends on the desired article for fabrication. In one embodiment, the cartridge is attached to the bioprinter through a carriage. In another embodiment, the cartridge is attached to a center piece which is attached to one or more carriages. In a further embodiment, the cartridge is attached to a center piece along the x-axis.

In one embodiment, one cartridge is utilized. In this instance, all of the components of the composition are combined in the single cartridge.

In another embodiment two or more, three or more, four or more, five or more, six or more, seven or more, eight or more, nine or more, or ten or more, i.e., multiple cartridges are utilized. In a further embodiment, 2 to 25 cartridges are used, for example, 2, 3, 4, 5, 6, 7, 8, 9, 10, 11, 12, 13, 14, 15, 16, 17, 18, 19, 20, 21, 22, 23, 24, or 25 cartridges. In this instance, each cartridge contains the same or different composition as other cartridges. For example, if using two cartridges, a unique composition may be deposited separately from each of the two cartridges. By doing so, the simultaneous or separate use of multiple cartridges may be used to create complex, hierarchical structures.

A single cartridge may be attached to one or more additional cartridges. Alternatively, a cartridge is position separately from the other cartridges.

The cartridge is made from any material which may be used in the bioprinter described herein. In one embodiment, the cartridge comprises glass, plastic, metal, gel, or any combination thereof. The cartridge may be coated on its interior or exterior with a casing. The casing may comprise any material that is compatible with the cartridge and comprises glass, metal, plastic, or a combination thereof. The casing may be the same material as the cartridge or different materials.

The cartridge is of any shape which fits into the bioprinter and may be selected by one skilled in the art. In one embodiment, the cartridge is cylindrically shaped. In another embodiment, the cartridge is graduated at one end, i.e., conical in shape.

FIG. 10 illustrates a cartridge system 1000. Cartridge system 1000 is configured to control light, temperature, or a combination thereof. The center of the cartridge inlet 1005 is configured to accept contents (e.g. biomaterial or biological material) directly or a syringe that can hold the contents. The content or syringe makes contact with center canister 1030 which can transfer heat. The heater (e.g., pelti heater) 1035 is configured to contact the center canister 1050 and the heat sinks 1060. The heat sinks 1060 further make contact with fans 1065 that are bolted to the to heat sinks 1060 with screws 1050, or glue or other attachment means could be used. Cartridge 1000 comprises a light 1040 underneath to control materials that require cross linking at a desired wavelength of electromagnetic radiation. The temperature and light are controlled through an electronics board 1020 attached to the center with screws 1015.

FIG. 11 illustrates cartridge system 1100. Cartridge system 1100 is configured to control light, temperature or a combination thereof. The center of the cartridge inlet 1005 is configured to accept the contents (e.g., biomaterial) directly or a syringe 1001 that can hold the contents of interest. These contents or syringe is configured to contact center canister 1115, which can transfer heat. The heat sinks 1140 then make contact with center canister 1115 and heat sinks 1160. The heat sinks 1140 further make contact with the fans 1130 that are screwed into the heat sinks 1140 with screws, glue or other attachment means. The cartridge 1100 comprises a light 1125 (e.g., LED) to control materials that require cross linking at a desired wavelength of electromagnetic radiation. The temperature and light are controlled through an electronics board 1120 attached to the center with screws 1105. The board can be controlled with a pin connection to upload new firmware 1110.

FIG. 12 illustrates an exploded view of cartridge system 1200. Cartridge system 1200 illustrates heat sink 1205 and 1245, fans 1270, pelti cooler 1255, center canister syringe 1275, lower LED board 1260, and syringe 1201 combined to achieve a cartridge system.

A syringe 1201 can be placed into a center canister 1275 that is the main center point to accept and transfer heat either towards or away from the canister. The canister is held in place by two high temperature brass brackets 1280 and further surrounded by pelti coolers 1255 and fans 1270 in the front that transfer heat ether towards or away from center canister 1275. The brass heat sinks 1205 and 1245 absorb the heat more rapidly. The brass brackets 1280 further transfer heat from the heat sinks 1205 and 1245 to the outer shell 1210 that provides both aesthetics as well as function. An LED board that can hold LEDs of wavelengths greater than 405 nm of electromagnetic radiation is stationed at the bottom of the extruder 1260 and is held in place by an outer shell 1265. The center components are then further held together by two pieces, a top piece 1215 and a bottom piece

1290. The electronics board 1250 controls and regulates the extruder is held in the back and attached with screws to the back bracket 1280. The cartridge further comprises an attachment mechanism 1285 that allows it to detach from a center printer piece. The attachment mechanism 1285 has two symmetrical arms 1230 of which a user can squeeze to attach or detach the extruder. These arms when pushed, further pushes another piece 1225 that latches on the center mount that initiates the attachment mechanism to disengage from the center mount. The attachment mechanism comprises springs 1235 that push the arms back out and the attachment mechanism into its engaged position. There is a piece that cover springs 1235 and the attachment mechanism 1240.

The cartridge 1200 further comprises a chamber and at least two openings. The cartridge 1200 has a capacity (i.e., a volume) which is dependent of the selected fabricated article, composition, and size of the delivery device. In one embodiment, the cartridge has a diameter of about 1 mm to about 100 mm. In another embodiment, the cartridge has a diameter of about 1 mm to about 10 mm. In a further embodiment, the cartridge has a capacity of at least about 0.1 ml. In another embodiment, the cartridge has a capacity of about 0.1 ml to about 5000 ml. In still a further embodiment, the cartridge has a capacity of about 1 ml to about 100 ml. In yet another embodiment, the cartridge has a capacity of about 1 ml to about 20 ml. In one embodiment, the cartridge contains one opening at one end and a second opening at the opposite end. In another embodiment, the cartridge contains one opening which permits insertion of a delivery device into the chamber. In a further embodiment, the cartridge contains a second opening which permits a portion of a delivery device, i.e., the needle, to exit the cartridge. The size of the first and second openings depends on the delivery device utilized in fabrication of the article. In one embodiment, the first and second openings are, independently, about 1 mm to about 10 mm. In another embodiment, the first and second openings are, independently, about 2 mm to about 10 mm.

Cartridge 1200 can be modified to accept syringes of all sizes, for example, 1 ml, 2.5 ml, 5 ml, 10 ml, 20 ml, or 50 ml.

The cap of the cartridge may attach directly to the cartridge and may attach thereto via one or more cap holders. The cap holder(s) attach to the cartridge. The cap is also compatible with the cap holder and securely fit together to substantially seal the cartridge. In one embodiment, the cap, cap holder, and the cap/cap holder secured together have grooves and ridges, i.e., a specific shape. Conversely, the center piece has the opposite grooves and ridges to that of the cap, cap holder, and/or cap/cap holder secured together.

The cartridge is secured into the center piece using known methods in the art. In one embodiment, the cartridge is secured into the center piece using mechanical force, electromagnetic force, or pressurized force. In another embodiment, the cartridge is secured into the center piece using one or more latches. In a further embodiment the cartridge is secured into the center piece using magnetic attraction, collet chuck grip, ferrule, nut, barrel adapter, or a combination thereof. The cartridge may be clipped or snapped in (manually or with magnetic force) or a robotic arm can be used to replace each cartridge in the limited number of cartridges as the printing proceeds. Compression may be applied to the center piece, cartridge, or any combination thereof to create a seal. In one embodiment, the seal prevents unwanted gases or solid particles from entering the cartridge. In another embodiment, the seal assists in the deposition of the composition. The compression may be applied manually or may be automated.

The bioprinter may also comprise a sensing means for sensing if the cartridge is locked into the center piece. In one embodiment, the sensing means is a magnetic sensor, electrical signal, mechanical switch, or a combination thereof. The sensing means may further include an alert if the cartridge is not locked into the center piece. In one embodiment, the sensing means is a light sensor, alarm, or a combination thereof. In another embodiment, the alert is generated using a light gate or a motion sensor.

The cartridge may be permanently or temporarily marked (e.g., with a pen or sticker), colored, dyed, scored, painted, polished, or any combination thereof. The cartridge may be uncovered, partially covered or fully covered using any means known in the art. In one embodiment, the cartridge prevents the contents therein from being prematurely exposed to the electromagnetic radiation (i.e., exposed to light). In another embodiment, the cartridge is covered to present premature EMR exposure. In a further embodiment, the cartridge is impermeable to light having a wavelength of about 405 nm or greater. In doing so, the covering prevents the composition from curing in the cartridge and jamming the delivery device, i.e., the syringe. Any part of the cartridge may be covered including, without limitation, the entire cartridge, the tip of the cartridge, a portion of the cartridge, or any combination thereof. In another embodiment, the cartridge is covered using aluminum foil, adhesive foil, a plastic film such as a Parafilm® coating, or the like.

Dispensing Means Using a Delivery Device

The cartridge disclosed herein houses and protects a delivery device. Many types of delivery devices are suitable for use with bioprinters disclosed herein and the methods of using the same. One of skill in the art would recognize that different delivery devices are required for different compositions containing a biomaterial. For example, certain compositions may degrade plastic and, in that case, glass or metal delivery devices may be used.

The delivery devices comprise one or more orifices through which the composition exits the cartridge. In one embodiment, the delivery devices comprise a single orifice. The orifice must be large enough to permit dispensing the composition, but not too large as to have uncontrolled dispensing of the composition. The shape of the orifice is not a limitation and may be, without limitation, flat, circular, square, rectangular, triangular, oval, polygonal, irregular, smooth or textured. Accordingly, selection of a suitable orifice depends on multiple factors, including, for example, the components and viscosity of the composition. In one embodiment, the orifice has a diameter of about 1 to about 1000 or more μm. In another embodiment, the orifice has a diameter of about 1 μm to about 100 μm.

The delivery device may be a capillary tube, a micropipette, syringe or a needle. In one embodiment, the delivery device contains a needle having a luminal diameter of about 1 mm to about 5 mm. In another embodiment, the delivery devices comprise a needle having a luminal diameter of about 1 mm to about 10 mm. In a further embodiment, the delivery device contains a needle of about 1 mm to about 300 mm in length. In yet another embodiment, the needle is about 10 mm to about 100 mm in length. In still a further embodiment, the delivery device is a Luer-Lok® Tip sterile syringe. In another embodiment, the delivery device has a ⅕ ml graduation. In a further embodiment, the delivery device has an about 6 mm (0.25") high precision tip.

FIGS. 13A-13D illustrate how one or more extruders can achieve a layer by layer addition by depositing 1310 the material out of a syringe 1305 within the cartridge 1300 and achieve a thick printed construct by growing many layers 1315.

The contents of the delivery devices may be optionally primed prior to use to increase the accuracy of the process. The priming includes making the contents of the delivery devices ready to be dispensed.

The delivery devices may be disposable or non-disposable (e.g., permanent). In one embodiment, the delivery devices are ejected or removed, automated or manually, from the bioprinter following extrusion, dispensing, or deposition of the contents. In another embodiment, a new dispensing means is attached to the bioprinter. In a further embodiment, the cartridge is a premixed and pre-sealed cartridge which contains a composition. By doing so, the user may purchase a cartridge and would not need to refill the delivery device by preparing and adding the composition.

The dispensing rate of the delivery device is dependent on one or more factors that will be readily apparently to those skilled in the art. In one embodiment, the dispensing rate is dependent on multiple factors, such as the viscosity of the composition. In another embodiment, the dispensing rate is dependent on the pressure applied to the composition. In a further embodiment, the dispensing rate is high so that a fine line of composition may be deposited. In yet another embodiment, the dispensing rate is low so that a thicker line of composition may be deposited. In other words, the dispensing rate is inversely proportional to the amount of composition deposited.

The delivery device may be sealed for ease of use and/or to avoid contamination of the contents therein. Alternatively, the delivery device is not sealed and may be opened by the user. In one embodiment, the delivery device is sealed using a cap or cap-like structure which is permanently affixed to the delivery device and cannot be pierced using a needle or the like. In another embodiment, the delivery device is sealed using a cap or cap-like structure which is permanently affixed to the delivery device, but the cap may be pierced with a needle by the user. In a further embodiment, the delivery device is sealed using a cap which may be easily removed by the user. In another embodiment, the delivery device is impermeable to electromagnetic radiation. In one embodiment, the delivery device is impermeable to electromagnetic radiating having a wavelength of about 405 nm or greater.

Extrusion Means

The composition passes through the delivery device using systems known in the art. In one embodiment, the composition is deposited onto the receiving device using gravity. In another embodiment, deposition of the composition may be facilitated via the use of an extrusion means. The term "extrude" or variations thereof as used herein refers to the ability of a composition to exit the delivery device.

For example, as one option, the extrusion means is a pressure means for controlling the pressure provided to the cartridge, delivery device, or any combination thereof. The pressure may be generated using any system known in the art including, without limitation, pneumatic systems using compressed gas such as compressed air, argon, carbon dioxide, or nitrogen, hydraulics, pistons, screw-based means, or any combination thereof. The pressure required to deposit the composition depends on multiple factors, such as the article being fabricated and the contents of the composition. In one embodiment, the pressure is about 50 kPa to about 1500 kPa (about 0.1 to about 150 psi). In one embodiment, the compressor which directs the gas at the delivery device and/or cartridge is connected to and operatively associated with the cartridge. By doing so, a controller and a pressure pump is provided for the delivery device. The pressure from the compressor drives deposition of the composition onto the receiving device. The pressure may be controlled using a dial operatively connected to the compressor. If more than one compressor is used, one dial may control the pressure of the compressor(s). Two or more dials may be utilized in an effort to obtain different pressures in different cartridges. In one embodiment, the compressed gas is fed into the cartridge and/or syringe using a hose. Each cartridge may utilize the same pressure to dispense the contents therein or use varying pressures.

Figure 16:
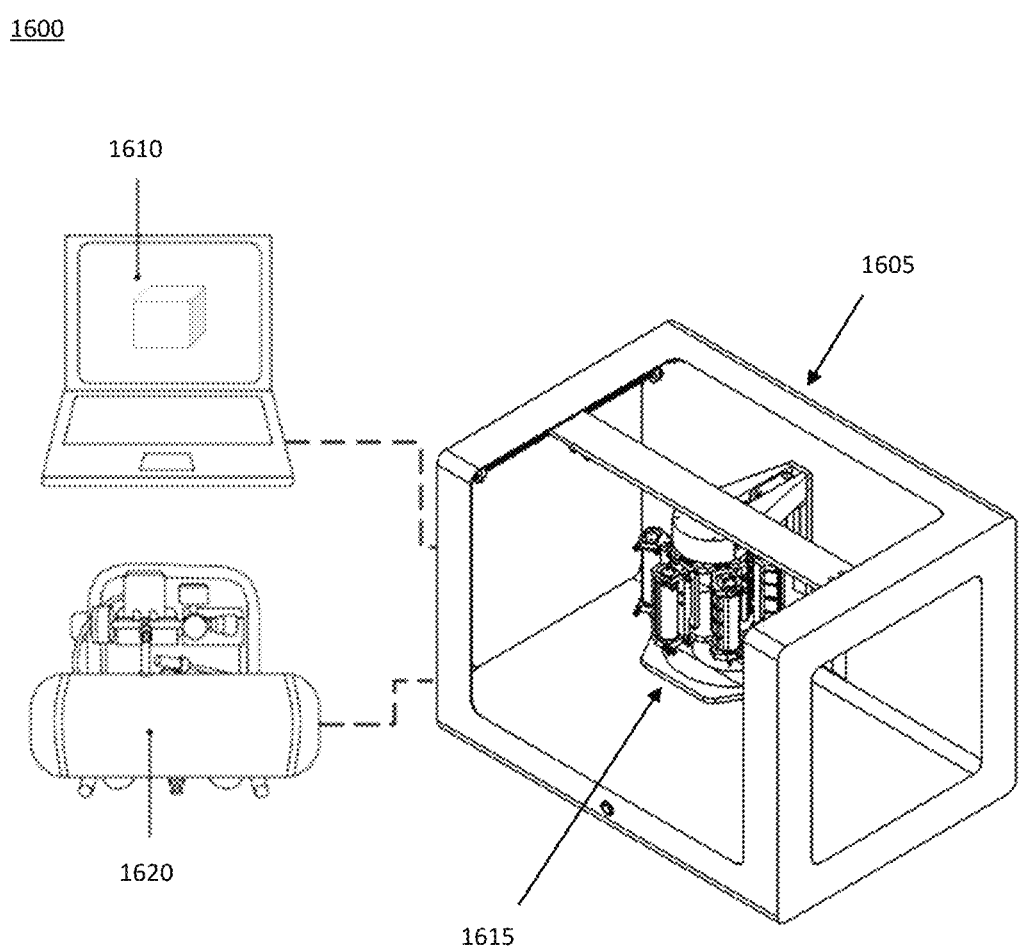
FIG. 16 illustrates an embodiment of a bioprinting system described herein.

FIG. 16 is a schematic of a system and apparatus provided herein. The system 1600 comprises computer 1610, air compressor 1620, and bioprinter 1605. Air compressor 1620 is connected to and operatively associated with cartridge to provide a controller and pressure pump for the syringe. The pressure from air compressor drives deposition of biomaterial onto receiving plate 1615. All components can be controlled by CAD software programmed in computer 1610.

The extrusion means may also be thermal, electrical, piezoelectric, or mechanical as determined by those skilled in the art. In one embodiment, heat is applied to the composition, thereby reducing its viscosity. In another embodiment, the composition is electrically charged using a current. In a further embodiment, the composition is extruded using piezoelectric methods. In yet another embodiment, the composition is extruded using mechanical means such as a screw system to drive deposition.

Optical Device

The bioprinter described herein may optionally include an optical device for viewing the fabricated article. In one embodiment, the optical device comprises a lens. In some embodiments, the lens comprises a blue filter. By doing so, the fabricated article may be viewed and/or recorded without interference from the EMR, thereby providing increased quality control in monitoring and/or preparing the article. In another embodiment, the optical device is an optical recorder such as a camera, video camera, heat sensor camera, or any combination thereof. The optical device is at a resolution (e.g., about 2× to about 100× magnification) that is required for the particular composition and article being fabricated. Accordingly, the resolution of the optical device may be low, medium, or high, as determined by those skilled in the art.

The optical detector may be placed at any appropriate location of the bioprinter. In one embodiment, the optical device is placed in close proximity to the fabricated article. In another embodiment, the optical device is mounted on one or more component of the bioprinter or is adapted to move along side of the receiving device and/or cartridge. In a further embodiment, the optical device is mounted on the cartridge, receiving device, in the corner of the bioprinter, among others. In another embodiment, the optical device is mounted on the cartridge. In a further embodiment, the optical device is mounted adjacent to the receiving device. In yet a further embodiment, the optical device is mounted on the cartridge facing the receiving device. In still another embodiment, the optical device is adapted to move inside of the bioprinter by way of a track or the like.

The optical device may be temporarily or permanently attached to one or more component of the bioprinter. In one embodiment, the optical device is attached to the EMR module. In another embodiment, the optical device is permanently attached to the EMR module. In a further embodiment, the optical device is reversibly attached to the EMR module. EMR modules are described in U.S. Pub. No. 2017/0172765, the contents of which are hereby incorporated by reference in their entirety.

A camera, for example, could be placed under the piston extruder to be able to take images of printed structures and provide resolution feedback. These images could be aggregated to understand patterns and trends from both the behavior of the printer as well as printing results.

Software

The bioprinter deposits the composition at precise locations (in two or three dimensions) on the receiving device. The locations are dependent on the form being prepared and inputted information, which is translated into computer code. As known in the art, the computer code is a sequence of instructions, executable in the central processing unit (CPU) of a digital processing device, and written to perform a specified task. Additional bioprinting parameters including, without limitation, height of the cartridge, pump speed, robot speed, control of variable delivery device, EMR exposure time, cartridge position, direction of the cartridge, and speed of the cartridge, among others.

Computer aided design software may be utilized to prepare the tissue constructs. In one embodiment, the software is 3D software. In another embodiment, the software is in the STL format. One of skill in the art would be able to select suitable software for use herein including 3DCrafter, 3DS Max, 3Dtin, Alibre, AC3D, Anim8or, Art of Illusion, AutoQ3D, AutoCAD, Blender, BRL-CAD, Cheetah3D, Cloud9, Creo Elements/Direct, DrawPlus, FormZ, FreeCAD, GLC Player, Google SketchUp, K-3D, LeoCAD, Maya, Magics, MeshLab, NetFabb, OpenSCAD, Rhino3D, Solidworks, STL-viewer, Tinkercad, Wings 3D, ZBrush, among others. The construct may be prepared from the top, the bottom, or the side as determined by one skilled in the art. In one embodiment, the construct is designed from the bottom.

The Slicer that is important to be able to take a 3D file created on one of the programs above and convert into a code that the printer can understand. The Slicer can be included in the software and only display parameter such as layer height, print speed, and nozzle diameter that are relevant for the demonstrated 3D printer.

The software may also be adapted to include code to modulate one or more component of the bioprinter. In one embodiment, the software modulates the flow of gas into the cartridge. In another embodiment, the software modulates the solenoid value that controls the flow of gas. In a further embodiment, the software controls the opening and closing of the solenoid value that controls the gas flow.

Alternatively or in conjunction, the tissue construct may be designed via reconstruction of tissues using medical imaging modalities. Examples of medical imaging modalities include, without limitation, Magnetic Resonance Imaging (MRI) and Computed Tomography (CT).

Non-Transitory Computer Readable Storage Medium

The devices, systems, and methods may further include non-transitory computer readable storage media or storage media encoded with computer readable program code. The computer readable storage medium may be connected to a bioprinter or removable from a digital processing device. Examples of computer readable storage medium include CD-ROMs, DVDs, flash memory devices, solid state memory, magnetic disk drives, magnetic tape drives, optical disk drives, cloud computing systems and services, among others.

Computer Modules

The devices, systems, and methods may include software, server, and database modules. As known in the art, "computer module" is a software component that interacts with a larger computer system, is one or more files and handles a specific task.

A computer module is optionally a stand-alone section of code or, optionally, code that is not separately identifiable. In some embodiments, the modules are in a single application. In other embodiments, the modules are in a plurality of applications. In some embodiments, the modules are hosted on one machine. In other embodiments, the modules are hosted on a plurality of machines. In some embodiments, the modules are hosted on a plurality of machines in one location. In other embodiments, the modules are hosted a plurality of machines in more than one location. Further described herein is the formatting of location and positioning data. In some embodiments, the data files described herein are formatted in any suitable data serialization format. A key feature of a computer module is that it allows an end user to use a computer to perform the identified functions.

Graphic User Interface

The computer module may include a graphic user interface (GUI) which provides a picture and/or text and may be 2- or 3-dimensional. The GUI may be a touchscreen or multitouchscreen. The GUI may include a grid comprising regularly spaced objects of substantially the same shape and substantially equal size.

The GUI may also be used to control one or more bioprinter parameter. In one embodiment, the GUI is used to control one or more components of the bioprinter. In another embodiment, the GUI is used to control the EMR, deposition speed, and/or temperature of one or more component, environmental conditions of one or more component, optical device, among others.

Components of the Composition

The tissues, organs, and vascular vessels may be prepared using the devices, systems, and methods described herein together with a composition. In one embodiment, the composition contains a biomaterial and optional additional components such as support material, non-cellular materials which enable bioprinting, or any combination thereof.

The composition may be prepared by mixing the cells and a biocompatible liquid or gel in a pre-determined ratio. The composition may optionally be treating to facilitate extrusion onto the receiving device, increase deposition efficiency, or initiate curing. In one embodiment, the composition is treated prior to extrusion to provide a desired cell density, provide a desired viscosity, among others using techniques known in the art. Such methods which may be utilized to prepare the composition for extrusion include, without limitation, centrifugation, tangential flow filtration, electrical conductance, light, or any combination thereof. The possible combinations of the components may vary. However, the components do not need to be mixed into one cartridge.

Biomaterial and Biological Materials

The term "biomaterial" includes any substance to interact with biological systems for any purpose. The term "biological material" includes any material or substances of which cells are composed. Biomaterials and biological materials can be a liquid, semisolid, or solid. Examples of biological materials include, for example, cell lysates, proteins, genes, peptides, antibodies, growth factors, biochemicals, or any combination thereof. In one embodiment, a composition comprises a biomaterial and a biological material. In one embodiment, the biomaterial and/or the biological material is viably maintained in a composition. In another embodiment, the biomaterial and/or the biological material withstands the shear forces utilized in the methods described herein. Any cell is suitable for use in a biomaterial as determined by those skilled in the art. The composition may contain only one biomaterial or more than one biomaterial. The composition may contain only one biological material or more than one biological material. In one embodiment, the cell is a mammalian cell, a plant cell, a bacterial cell or a combination thereof. In another embodiment, the biological material comprises a viral capsid.

Examples of cells include, without limitation, cells in suspension solution, cells by themselves, cells with hydrogels, multicellular solutions with or without hydrogel, tissues, or any combination thereof. A number of cells may be selected and include differentiated and undifferentiated cells. In one embodiment the cells include, without limitation, contractile or muscle cells (e.g., skeletal muscle cells, cardiomyocytes, smooth muscle cells, and myoblasts), connective tissue cells (e.g., bone cells, cartilage cells, fibroblasts, and cells differentiating into bone forming cells, chondrocytes, or lymph tissues), bone marrow cells, endothelial cells, skin cells, epithelial cells, breast cells, vascular cells, blood cells, lymph cells, neural cells, Schwann cells, gastrointestinal cells, liver cells, pancreatic cells, lung cells, tracheal cells, corneal cells, genitourinary cells, kidney cells, reproductive cells, adipose cells, parenchymal cells, pericytes, mesothelial cells, stromal cells, undifferentiated cells (e.g., embryonic cells, stem cells, and progenitor cells), endoderm-derived cells, mesoderm-derived cells, ectoderm-derived cells, and any combination thereof.

A "stem cell" as used herein refers to mitotic cells which can differentiate into other cells. Stem cells may include, without limitation, totipotent cells, pluripotent cells, multipotent cells, oligopotent cells, and unipotent cells. Stem cells may include embryonic stem cells, perinatal stem cells, adult stem cells, amniotic stem cells, and induced pluripotent stem cells.

Accordingly, the methods and systems described herein are useful in generating tissue, organs, and vascular tubes. "Tissue" as used herein refers to a grouping of cells of the same type that perform a specific function. Examples of tissues include, but are not limited to, connective (loose-areolar, reticular, and adipose and dense-regular and irregular), muscle (e.g., smooth, skeletal, and cardiac), nervous tissue (brain, spinal cord, and nerve), and epithelial (shape and arrangement classified), and special connective (cartilage, bone, blood). In one embodiment, intraluminal fluid perfusion may be used during the preparation of vascular tubes to mimic blood pressures.

An "organ" is a collection of tissues in a specific structure to perform a function. Examples of organs include, but are not limited to, skin, sweat glands, sebaceous glands, mammary glands, muscle, cartilage, bone marrow, bone, brain, hypothalamus, pituitary gland, pineal body, heart, blood vessels, cornea, heart valve, larynx, trachea, bronchus, lung, lymphatic vessel, salivary glands, mucous glands, esophagus, stomach, gallbladder, liver, pancreas, small intestine, large intestine, colon, urethra, kidney, adrenal gland, conduit, ureter, bladder, fallopian tube, uterus, ovaries, testes, prostate, thyroid, parathyroid, meibomian gland, parotid gland, tonsil, adenoid, thymus, and spleen, teeth, gums, hair follicle, trachea, cartilage, or any combination thereof.

The cell density necessary for the composition is dependent on multiple factors, including the cells utilized and article being fabricated. The cells may be pre-treated prior to incorporation into the composition using techniques such as incubation. The cells may also be maintained at a selected temperature. In some embodiments, the cells are frozen, the cells are maintained at a lower temperature, the cells are maintained at an ambient temperature, or the cells are maintained at a temperature greater than an ambient temperature. In one embodiment, the cells are at about 37° C. or greater. In a further embodiment, embodiment, bacterial cells are at about 37° C. or greater. In another embodiment, the cells are maintained at lower temperatures prior to, during or after printing.

Extrusion Agent

One or more extrusion agent may further be added to the composition described herein. In one embodiment, the extrusion agent cures, thereby encapsulating the biomaterial during formation of the fabricated article. The term "cure" or variations as used herein is utilized to describe the process for toughening or hardening one component of the composition described herein via the crosslinking of the components. In one embodiment, the curing occurs concurrently as the bioprinting proceeds (i.e., the curing and bioprinting occur simultaneously). The length of time required for the curing to complete depends on the components of the composition, article to be fabricated, and/or laboratory conditions, among others. In one embodiment, curing is complete in less than about 1 year. In another embodiment, curing is complete in about 1 second to about 1 year. In a further embodiment, curing is complete in about 1 second to about 1 minute.

The extrusion agent may cure in the absence of exogenous agents or techniques. In one embodiment, the extrusion agent is cured using electron beams, heat or chemical additives such as one or more photo-initiator as described below. In a further embodiment, the extrusion agent is curable at a wavelength of about 405 nm or greater.

In one embodiment, the extrusion agent is a support material. Two or more support materials, i.e., 2 to about 20, may be included in the composition. The support material is selected based on the desired quality, viscosity, permeability, elasticity or hardness, adherency, biocompatibility, 3D printed structure, or the like. The support material is capable of hardening, viscous, excludes cells from growing or migrating into or adhering to it, or any combinations thereof. In one embodiment, the support material is curable or cross-linkable at a wavelength of about 405 nm or greater. The support material is optionally removed prior to use of the fabricated article. In one embodiment, the support material is removed via dissolution. Accordingly, the support material may be water-soluble, organic solvent soluble, dissolvable via enzymatic degradation, or dissolvable under acidic or basic conditions. In one embodiment, the enzymatic degradation is performed using a protease or lipase. The protease is, without limitation, proteinase K, protease XIV, a-chymotrypsin, collagenase, matrix metalloproteinase-1 (MMP-1), MMP-2, or any combination thereof. The dissolution may alternatively be performed using cations.

A variety of support materials may be selected by one skilled in the art using the instant specification. In one embodiment, the support material is a polymer. In another embodiment, the support material is a thermoplastic polymer. In a further embodiment, the support material is polyethylene oxide, poly-caprolactone, poly(L)-lactic acid (PLLA), or gelatin methacrylate, or any combination thereof. In yet another embodiment, the polymer is, without limitation, diacrylates such as polyacrylic acid or polyethylene glycol diacrylate, methacrylates such as hydroxyethyl methacrylate, norborenes, hydrogel, NovoGel™, gelatin, Matrigel™ hyaluronan, poloxamer, peptide hydrogel, poly(isopropyl-n-polyacrylamide), polydimethylsiloxane, polyacrylamide, poly lactic acid, silicon, silk, surfactant polyols, thermo-responsive polymers, hyaluronates, alginates, collagens, nanofibers, self-assembling nano fibers, hydrogels derived from collagen, hyaluronate, fibrin, agarose, chitosan, poly(ethylene oxide), polyvinyl alcohol, polyphosphazene, or derivatives, copolymers or any combination thereof. In yet a further embodiment, the diacrylate is PEG-DA. In still another embodiment, the methacrylate is PEG-MA. In a further embodiment, the norbomene is PEG-norbomene. In another embodiment, the polyoxyethylene is poly(ethylene glycol). One of skill in the art would be able to determine a suitable ratio of support material to cells depending on the other components of the composition.

Photo-Initiator

To create healthy 3D tissues, damage to the cells by light (phototoxicity) should be minimized. Visible light reduces the energy that the tissues are exposed to. Thus, a photo-initiator also may be utilized in the composition described herein. In one embodiment, the photo-initiator promotes curing of the composition. In a further embodiment, the photo-initiator promotes cross-linking of one or more component of the composition. In another embodiment, the photo-initiator is a visible light photo-initiator. In a further embodiment, the photo-initiator is activated when exposed to blue light. In another embodiment, the photoinitiator is lithium phenyl-2,4,6-trimethylbenzoylphosphinate. In yet a further embodiment, the photo-initiator is the Irgacure™ 2959 product which contains one or more of the following:

The ratio of the polymer to the photo-initiator is dependent on the selection of the polymer for use as described herein. The amount of photo-initiator must be sufficient to initiate cross-linking of the polymer. In one embodiment, the weight ratio of the polymer to the photoinitiator is about 1:1 to about 20:1.

Other Components

The composition may optionally contain additional agents to facilitate preparation of the desired product. One of skill in the art would readily be able to select suitable additional agents for use herein.

In one embodiment, the composition includes an extracellular matrix. Examples of extracellular matrix components include, without limitation, collagen, fibronectin, laminin, hyaluronates, elastin, proteoglycans, gelatin, fibrinogen, fibrin, or any combination thereof. The noncellular components of the composition may be retained or may be removed prior to use using physical, chemical, or enzymatic means.

In a further embodiment, the composition includes a wetting agent as described above.

In yet a further aspect, the composition includes a cell-binding factor. Examples of cell-binding factors useful herein include, without limitation, fibronectin, lectins, cadherins, claudins, laminin, or any combination thereof.

In another embodiment, the composition includes an antioxidant. Examples of antioxidants include, without limitation, buffers such as phosphate buffered saline.

In a further embodiment, the composition includes an agent that inhibits cell death. Examples of agents that inhibit cell death include those that inhibit the activity of an interleukin, interferon, granulocyte colony-stimulating factor, macrophage inflammatory protein, transforming growth factor B, matrix metalloproteinase, caspase, MAPK/JNK signaling cascade, Src kinase, Janus kinase, or any combination thereof.

In yet another embodiment, the composition includes an agent that encourages cell adhesion. Examples of an agent that encourages cell adhesion include, without limitation, Arginine-Glycine-Aspartic Acid (RGD), integrin, and extracellular matrix (ECM).

In still a further embodiment, the composition includes polyoxypropylenes and polyoxyethylenes.

In another embodiment, magnetic fields may be used to guide cellular reorganization and migration of the various cell types. Accordingly, the compositions may contain magnetic particles such as ferromagnetic nanoparticles, and are subjected to magnetic fields to guide cellular reorganization and migration.

A viscosity agent may optionally be added to the composition. By doing so, maintenance or fidelity of the extruded layer may be achieved due to the imparted sufficient cohesive forces within the composition. In one embodiment the selected viscosity agent depends on the shear thickening or thinning of the components of the composition. In a further embodiment, the viscosity agent ensures that the composition is sufficiently viscous to maintain its shape when extruded. In another embodiment, the viscosity agent ensures that the composition is not too thick so as to prevent its extrusion. In one embodiment, the viscosity agent is poly(ethylene oxide), gelatin, Pluronic F-127 (i.e., a (polyethyleneoxide)-(polypropyleneoxide)-(polyethyleneoxide) based material), hyaluronic acid, or any combination thereof.

Fabricated Article

As discussed above, the methods, devices, and systems described herein permit the fabrication of a variety of articles using EMR at a wavelength of about 405 nm or greater. Accordingly, the fabricated article contains one EMR responsive material and cells as described above.

In one embodiment, the article is a cellular construct. In another embodiment, the article is 3-dimensional. In another embodiment, the article is a tissue construct such as an organ. In a further embodiment, the article is an array of cells. In still a further embodiment, the article is any body part (i.e., an organ) or organic structure to enhance and/or mediate bodily functions. In yet another embodiment, the article is a splint for implantation into a mammal, button (e.g., plug, stopgap, filling), among others.

The organ may be any component of a mammal. In one embodiment, the organ is skin, sweat glands, sebaceous glands, mammary glands, bone, brain, hypothalamus, pituitary gland, pineal body, heart, blood vessels, larynx, trachea, bronchus, lung, lymphatic vessel, salivary glands, mucous glands, esophagus, stomach, gallbladder, liver, pancreas, small intestine, large intestine, colon, urethra, kidney, adrenal gland, conduit, ureter, bladder, fallopian tube, uterus, ovaries, testes, prostate, thyroid, parathyroid, meibomian gland, parotid gland, tonsil, adenoid, thymus, spleen, teeth, gums, hair follicle, or cartilage.

A variety of plants or parts thereof may be printed using the methods and systems described herein. In one embodiment, the plant is algae, a plant which produces a natural product, an agricultural plant designed for human or animal ingestion, among others.

Bacterial and viral capsids may also be printed using the methods and systems described herein. In one embodiment, the bacterium is *Escherichia coli, streptococcus, Anaplasma, Bacillus-brevis*, Interrococcus, among others. In another embodiment, the viral capsid is Adenaassociated, Aichi, Australian bat lyssavirus, BK polyoma, Banna, Barmah forest, Bunyamwera, Bunya La Crosse, Bunya snowshoe hare, caudiovirales, Cercopithecine herpes, Chandipura, Chikungunya, Cosa A, Cowpox, Coxsackie, Crimean-Congo hemorrhagic fever, Dengue, Dhori, Dugbe, Duvenhage, Eastern equine encephalitis, Ebola, Echo, Encephalomyocarditis, Epstein-Barr, European bat lyssavirus, GB C/Hepatitis G, Hantaan, Hendra, Hepatitis A, Hepatitis B, Hepatitis C, Hepatitis E, Hepatitis delta, Horsepox, Human adena, Human astra, Human corona, Human cytomegalovirus, Human entero 68, 70, Human herpes 1, Human herpes 2, Human herpes 6, Human herpes 7, Human herpes 12 Jun. 22, 2017 8, Human immunodeficiency, Human papilloma 1, Human papilloma 2, Human papilloma 16, 18, Human parainfluenza, Human parvo B19, Human respiratory syncytial, Human rhino, Human SARS corona, Human spumaretro, Human T-lymphotropic, Human taro, Influenza A, Influenza B, Influenza C, Isfahan, JC polyoma, Japanese encephalitis, Jnnin arena, KI Polyoma, Knnjin, Lagos bat, Lake Victoria Marburg, Langat, Lassa, Lordsdale, Louping ill, Lymphocytic choriomeningitis, Machupo, Mayaro, MERS corona, Measles, Mengo encephalomyocarditis, Merkel cell polyoma, Mokola, Molluscum contagiosum, Monkeypox, Mumps, Murray valley encephalitis, New York, Nipah, Norwalk, O'nyong-nyong, Orf, Oropouche, Pichinde, Poli, Pnnta taro phlebo, Puumala, Rabies, Rift valley fever, Rosa A, Ross river, Rota A, Rota B, Rota C, Rubella, Sagiyama, Sali A, Sandfly fever sicilian, Sapporo, Semliki forest, Seoul, Simian foamy, Simian 5, Sindbis, Southampton, St. louis encephalitis, Tick-borne powassan, Torque teno, Toscana, Uukuniemi, Vaccinia, Varicella-zoster, Variola, Venezuelan equine encephalitis, Vesicular stomatitis, Western equine encephalitis, WU polyoma, West Nile, Yaba monkey tumor, Yaba-like disease, Yellow fever, or Zika, among others.

The fabricated article may have a single layer or multiple layers, depending on the desired use, and may be unicellular or multicellular. The fabricated article may also include repeating pattern of functional units. The functional unit may have any suitable geometry, including circles, squares, rectangles, triangles, polygons, and irregular geometries. The repeating pattern of bioprinted functional units may be in the form of layers, i.e., a base layer and one or more layers thereon. The orientation of the layers is dependent on the final article to be fabricated. In one embodiment, the layers may all be in the same direction, may vary in direction, or any combination thereof. In another embodiment, the layers form a pattern. In a further embodiment, the layers are alternating. In still another embodiment, the layers lack any pattern.

FIG. 14 illustrates samples of a print with 3 different layers and of how the printer can coordinate to print out a structure with different patterns.

FIG. 15 further illustrates a material with 6 prints and how one can begin to create a large variety of different geometrical arrangements to be able to achieve a desire construct of interest.

The fabricated article may be of any form which is useful to the attending clinician. In one embodiment, the fabricated article is a gel or solid.

The fabricated article may be formed by depositing a composition onto a receiving device. In one embodiment, the composition exits the orifice in the form of a droplet or stream. As described above, the composition cures after exposure to EMR of a wavelength of about 405 nm or greater.

Fabrication of the article may be continuous and/or substantially continuous. In one embodiment, fabrication of the article is continuous. In another embodiment, fabrication of the article is continuous with periods of inactivity. The fabricated article may be permitted sit for a sufficient time after formation, i.e., incubated. In one embodiment, the fabricated article sits so as to permit cell adhesion, reorganization migration, or any combination thereof. Additional methods for facilitating incubation may be performed utilized and include, without limitation, heating, cooling, pressure, tension, compression, mechanical forces, humidity changes, or any combination thereof.

At the end of the incubation period, the cells may be isolated by removing any non-essential components. In one embodiment, any unwanted components such as the support medium and/or extrusion agent is removed. In another embodiment, the support medium is physically removed away from the support medium. In another embodiment, the support medium is removed using water or any solvent that the non-cellular material is soluble in.

Finally, the fabricated article, lacking any nonessential components, may be finalized by permitting the cells to mature. In one embodiment, the fabricated article is place in a maturation chamber for growth.

Kits

Also provided are kits or packages containing any component of the bioprinter described herein. In one embodiment, the kit or package contains one or more of a bed plate, receiving device, cartridge, delivery device such as a syringe, capillary tube, or pipette, air compressor, EMR source, software, non-transitory computer readable storage medium, computer module, graphic user interface, optical device, among others, or any combination thereof.

The kit or package may also include one or more component of the composition. In one embodiment, the kit or package contains one or more biomaterial such as cells. In another embodiment, the kit or package contains one or more of an extrusion agent, photo-initiator, extracellular matrix, antioxidant, agent that inhibits cell death, agent that encourages cell adhesion, magnetic particles, viscosity agent, extrusion agent such as support material, among others, or any combination thereof.

The kit or package may further include one or more of a vial, tube, applicator, needle, delivery device, lid, sealant, foil, and other appropriate packaging and instructions for use.

The kit may contain one or more component of the composition. One or more component of the composition may be separate, two or more components may be combined, or any combination thereof. In one embodiment, all of the components of the composition may be combined in a single delivery device in the kit. In another embodiment, each component of the composition may be contained in a separate delivery device in the kit. In a further embodiment, some of the components are individually present in a delivery device and some of the components are combined in a single delivery device.

Methods of Using the Bioprinters

The bioprinters described herein and the fabricated synthetic, i.e., man-made articles produced thereby have a variety of uses. In one embodiment, the fabricated articles in the form of organs may be transplanted into a mammal in need thereof. The organs may be transplanted in the absence or presence of immunosuppressant agents as determined by the attending physician and transplanted organ. In one embodiment, immunosuppressant agent may be administered, prior to, concurrently with, or subsequent to the transplantation. In another embodiment, the anti-rejection agent is an induction, maintenance, immunosuppressant. In a further embodiment, the anti-rejection agent is, without limitation, atgam, azathioprine, basiliximab, cyclosporine, daclizumab, methylprednisolone, mofetil, muromonabCD3, mycophenolic acid, mycophenolate mofetil, OKT3, prednisone, rapamycin, sirolimus, tacrolimus, thymoglobulin, or any combination thereof. Additional agents may be administered prior to, concurrently with, and subsequent to the transplantation and include, without limitation, pain medications, among others.

The fabricated synthetic articles produced as described herein also have use in testing a wide variety of chemical agents. By doing so, the necessity to perform animal testing may be reduced or eliminated. Specifically, functions inherent to the particular cells of the fabricated articles may be evaluated, i.e., ensuring that the cells are properly functioning. Such functions include, without limitation, protein function, cell marker viability, cell adhesion, or cell contraction. Accordingly, the sensitivity, viability, toxicity, and resistance, among others, of the chemical agents may be evaluated. Accordingly, the fabricated synthetic articles produced herein have use in vitro tests across a number of industries. The term "chemical agent" as used herein refers to any single chemical or composition containing that chemical agent which must be tested prior to distribution to the public. In one embodiment, the chemical agent may be household chemicals, pharmaceuticals such as antibiotics and chemotherapeutic agents, environmental agents, agricultural chemicals, food additives, healthcare agents, among others. In doing so, the chemical agent may be applied to a cellular structure prepared using the bioprinters herein. After application, the cellular structure may be monitored. In one embodiment, the viability of the cells in the cellular structure may be monitored and measured as necessary.

What is claimed is:

1. A three-dimensional bioprinter comprising:
  a multi-headed printing system, wherein the multi-headed printing system comprises a plurality of cartridges, each of the cartridges reversibly mounted to a centerpiece of the multi-headed printing system,
  each of the cartridges comprising a temperature control unit, the temperature control unit comprising a Peltier element configured to maintain the contents of the cartridge at a constant temperature, and wherein each of the cartridges comprises a mechanical, an electrical or a pneumatic mechanism configured to extrude the contents of the cartridge onto a receiving device.

2. The three-dimensional bioprinter of claim 1, wherein the multi-headed printing system further comprises a plurality of linear motion carriages, wherein one of the plurality of linear motion carriages secure and allow vertical movement of one of the plurality of cartridges.

3. The three-dimensional bioprinter of claim 1, wherein the one or more temperature control units comprises a heating unit, a cooling unit, a thermoelectric unit, a fan, or a combination thereof.

4. The three-dimensional bioprinter of claim 1, wherein each of the plurality of cartridges is configured to receive a composition, wherein the composition comprises a biomaterial, a biological material, a curable extrusion agent or a combination thereof.

5. The three-dimensional bioprinter of claim 4, wherein the biological material comprises a cell, a protein, a biochemical, a growth factor or a combination thereof.

6. The three-dimensional bioprinter of claim 4, wherein the biomaterial comprises a hydrogel, a matrigel or a combination thereof.

7. The three-dimensional bioprinter of claim 4, wherein the cartridge comprises an LED board configured to produce electromagnetic radiation greater than 405 nm.

8. The three-dimensional bioprinter of claim 4, wherein each of the plurality of cartridges is sized and configured to receive a delivery device containing the composition.

9. The three-dimensional bioprinter of claim 8, wherein the delivery device is a syringe.

10. The three-dimensional bioprinter of claim 9, wherein the delivery device is configured to dispense the composition at a volume between about 0.1 µl to about 1000 µl.

11. The three-dimensional bioprinter of claim 9, wherein the delivery device is configured to extrude the composition for about 0.1 seconds to about 2 days.

12. The three-dimensional bioprinter of claim 1, wherein each of the plurality of cartridges further comprises a central canister.

13. The three-dimensional bioprinter of claim 12, wherein the central canister comprises a heat transfer material, and wherein the heat transfer material comprises copper, aluminum, or nickel.

14. The three-dimensional bioprinter of claim 3, wherein each of the plurality of cartridges further comprises one or more heat sinks, one or more fans, or a combination thereof.

15. The three-dimensional bioprinter of claim 14, further comprising an insulated electronics board, wherein the electronics board controls the temperature control for each of the cartridges.

16. The three-dimensional bioprinter of claim 1, comprising a reversibly mounted bed plate having a recessed area configured to accommodate the receiving device.

17. The three-dimensional bioprinter of claim 16, wherein the receiving device is a microtiter plate, a petri dish, or a glass slide.

18. The three-dimensional bioprinter of claim 16, wherein the bed plate comprises temperature control unit.

19. The three-dimensional bioprinter of claim 16, wherein the bed plate comprises an auto-calibration system, wherein the auto-calibration system comprises one or more electrical pads.

20. The three-dimensional bioprinter of claim 1, wherein each of the cartridges reversibly mounted to a centerpiece of the multi-headed printing system by at least one of a spring and latch attachment mechanism, or a magnetic attachment.

21. A cartridge assembly for use in a bioprinter, the cartridge assembly comprising:
  a cartridge inlet configured to receive a composition including a biomaterial, a biological material, a curable extrusion agent or a combination thereof;
  a central cannister configured to contact the cartridge inlet and provide heat to the contents of the cartridge inlet;
  a temperature control unit comprising a Peltier element configured to maintain the contents of the cartridge assembly at a constant temperature, wherein the temperature control unit is positioned to contact the center cannister, at least one heat sink and at least one fan configured to maintain the cartridge assembly at a constant temperature; and
  an attachment mechanism configured to engage the cartridge assembly with the bioprinter.

22. The cartridge assembly of claim 21, further comprising an electromagnetic radiation module (EMR) configured to emit electromagnetic radiation at or above 405 nm.

23. The cartridge assembly of claim 21, wherein the Peltier element is configured to maintain the temperature between about −20° C. to 150° C.

* * * * *